United States Patent
Igarashi

(10) Patent No.: US 11,712,497 B2
(45) Date of Patent: Aug. 1, 2023

(54) BLOOD BAG SYSTEM AND BLOOD TREATMENT METHOD

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Shizuoka (JP)

(*) Notice: Subject to any disclaimer, the term of this patent is extended or adjusted under 35 U.S.C. 154(b) by 1083 days.

(21) Appl. No.: 16/336,950

(22) PCT Filed: Sep. 26, 2017

(86) PCT No.: PCT/JP2017/034813
§ 371 (c)(1),
(2) Date: Mar. 27, 2019

(87) PCT Pub. No.: WO2018/062211
PCT Pub. Date: Apr. 5, 2018

(65) Prior Publication Data
US 2019/0231948 A1    Aug. 1, 2019

(30) Foreign Application Priority Data

Sep. 30, 2016    (JP) .............................. JP2016-192935

(51) Int. Cl.
*A61M 1/02*    (2006.01)
*A61M 1/36*    (2006.01)
*A01N 1/02*    (2006.01)

(52) U.S. Cl.
CPC ......... *A61M 1/0209* (2013.01); *A01N 1/0242* (2013.01); *A61M 1/0218* (2014.02);
(Continued)

(58) Field of Classification Search
CPC .............. A61M 1/0209; A61M 1/0218; A61M 1/0272; A61M 1/0295; A61M 1/3693;
(Continued)

(56) References Cited

U.S. PATENT DOCUMENTS 5,836,934 A * 11/1998 Beshel ................ A61M 1/0218
210/231
10,226,556 B2 * 3/2019 Schroeder ............. A61M 1/025
(Continued)

FOREIGN PATENT DOCUMENTS

EP    0600804 B1    8/1997
EP    2982393 A1    2/2016
(Continued)

OTHER PUBLICATIONS

Article 94(3) Communication for Europe Patent Application No. 17784025.3, dated Feb. 24, 2022, 6 pages.

*Primary Examiner* — Ariana Zimbouski
(74) *Attorney, Agent, or Firm* — Sheridan Ross P.C.

(57) ABSTRACT

Provided are a blood bag system and a blood treatment method capable of securely and efficiently obtaining a medium specific gravity blood component having a sufficiently low content rate of a light specific gravity blood component.

In a blood bag system (10) used for a blood treatment method, in a transfer completed state in which whole blood in a first bag (12) is centrifuged to transfer blood plasma to a second bag (14) through a first transfer tube (24) and transfer red cell concentrates to a third bag (16) through a second transfer tube (26), a buffy coat is left in the first bag (12). In the transfer completed state, when a platelet added solution is transferred from a fourth bag (18) to the first bag
(Continued)

(12) on which a centrifugal force acts through a third transfer tube (28), blood plasma in the buffy coat is discharged from the first bag (12).

20 Claims, 18 Drawing Sheets

(52) U.S. Cl.
CPC ........ *A61M 1/0272* (2013.01); *A61M 1/0295* (2014.02); *A61M 1/3693* (2013.01)

(58) Field of Classification Search
CPC . A61M 1/0213; A61M 1/3695; A61N 1/0242; B04B 5/0428; B04B 2005/0435
See application file for complete search history.

(56) References Cited

U.S. PATENT DOCUMENTS

| | | | |
|---|---|---|---|
| 2008/0234622 A1* | 9/2008 | Hlavinka | ............ A61M 1/3693 604/6.08 |
| 2009/0127206 A1 | 5/2009 | Hogbert et al. | |
| 2015/0209496 A1 | 7/2015 | Biset et al. | |

FOREIGN PATENT DOCUMENTS

| | | | | |
|---|---|---|---|---|
| EP | 2357012 B1 | 1/2019 | | |
| WO | WO-2015080918 A1 * | 6/2015 | .......... | A61M 1/0209 |
| WO | WO-2015097411 A * | 7/2015 | .......... | A61M 1/0209 |
| WO | WO 2016/134317 | 8/2016 | | |

\* cited by examiner

BLOOD BAG SYSTEM AND BLOOD TREATMENT METHOD

TECHNICAL FIELD

The present invention relates to a blood bag system and a blood treatment method for centrifuging whole blood or a blood component into a light specific gravity blood component, a medium specific gravity blood component, and a heavy specific gravity blood component.

BACKGROUND ART

Recently, in transfusion, component transfusion has been performed to separate a component of blood (whole blood) obtained by blood donation and the like and provide only a component required by a patient. According to the component transfusion, a burden on a circulatory system or a side effect may be reduced for the patient, and effective use of the donated blood is attempted.

In separation of a blood component, for example, a blood bag system including a plurality of bags and a plurality of tubes is attached to a centrifugation transfer device disclosed in Patent Literature 1 below. Further, the blood component is centrifuged into a supernatant PPP (platelet poor plasma) fraction corresponding to a light specific gravity blood component, a precipitated RCC (red cell concentrates) fraction corresponding to a heavy specific gravity blood component, and a buffy coat corresponding to a medium specific gravity blood component formed therebetween by the centrifugation transfer device. The respective centrifuged components are transferred to the plurality of bags and preserved.

CITATION LIST

Patent Literature

Patent Literature 1: WO 2014/162592 A

SUMMARY OF INVENTION

Technical Problem

Incidentally, at the time of transfusion of platelet preparation, there is a possibility that a patient may have a side effect of the transfusion. Blood plasma contained in the platelet preparation is considered as a cause of the side effect. For this reason, a platelet having a low blood plasma content rate (washed platelet: washed platelet concentrate) is desired at a transfusion site.

When such a washed platelet is refined, first, the buffy coat is centrifuged from blood using the above-described centrifugation transfer device. Subsequently, buffy coat pooling is performed to transfer and gather buffy coats in the plurality of bags to one bag. Then, a platelet added solution is added to the buffy coats obtained by the buffy coat pooling to replace blood plasma remaining in the buffy coats with the platelet added solution. Thereafter, the buffy coats containing the platelet added solution (washed buffy coats) are centrifuged into a platelet component and a red blood cell, and a white blood cell is removed from the platelet component using a filter, thereby obtaining the washed platelet.

However, a considerable amount of blood plasma (light specific gravity blood component) is contained in the buffy coat (medium specific gravity blood component) obtained by the above-described centrifugation. For this reason, in a method of replacing the blood plasma in the buffy coat with the platelet added solution, a washed platelet having a sufficiently low blood plasma content rate may not be efficiently obtained.

The invention has been conceived in view of the above problems, and an object of the invention is to provide a blood bag system and a blood treatment method capable of securely and efficiently obtaining a medium specific gravity blood component having a sufficiently low content rate of a light specific gravity blood component.

Solution to Problem

In order to achieve the object, a blood bag system according to the present invention includes: a first bag for storing whole blood or a blood component; a second bag and a third bag for storing two blood components, respectively, among a light specific gravity blood component, a medium specific gravity blood component, and a heavy specific gravity blood component obtained by centrifuging a content liquid in the first bag; a first transfer tube for connecting the first bag and the second bag to each other and transferring one blood component from the first bag to the second bag; and a second transfer tube for connecting the first bag and the third bag to each other and transferring the other blood component from the first bag to the third bag, wherein the blood bag system further includes: a fourth bag storing an added solution; and a third transfer tube for transferring the added solution from the fourth bag to a bag storing the medium specific gravity blood component, and a centrifugal force acts in a transfer completed state in which the two blood components are separately transferred to the second bag and the third bag, respectively, and the added solution is transferred from the fourth bag to the bag accommodating the medium specific gravity blood component through the third transfer tube, thereby discharging the light specific gravity blood component remaining in the medium specific gravity blood component to an outside of the bag.

According to such a configuration, since the light specific gravity blood component remaining in the medium specific gravity blood component in the transfer completed state may be discharged from the bag by the added solution, it is possible to obtain a washed medium specific gravity blood component. In this way, it is possible to securely and efficiently obtain a medium specific gravity blood component having a sufficiently low content rate of a light specific gravity blood component.

According to the blood bag system, in the transfer completed state, the medium specific gravity blood component may remain in the first bag, the light specific gravity blood component may be stored in the second bag, and the heavy specific gravity blood component may be stored in the third bag, and the third transfer tube may be a tube for transferring the added solution from the fourth bag to the first bag.

According to such a configuration, it is possible to efficiently store a medium specific gravity blood component having a sufficiently low content rate of a light specific gravity blood component in the first bag.

The blood bag system may include: a fifth bag that stores a waste liquid containing the light specific gravity blood component and the added solution discharged from the first bag; and a fourth transfer tube for transferring the waste liquid discharged from the first bag to the fifth bag.

According to such a configuration, since the waste liquid discharged from the first bag is stored in the fifth bag, the waste liquid may be easily treated.

According to the blood bag system, the third transfer tube may connect the second transfer tube and the fourth bag to each other, and the fourth transfer tube may connect the first transfer tube and the fifth bag to each other.

According to such a configuration, configurations of the first bag and the tube may be simplified.

The blood bag system may include: a first clamp that closes and opens a second bag side of a connecting portion connected to the fourth transfer tube in the first transfer tube; a second clamp that closes and opens a third bag side of a connecting portion connected to the third transfer tube in the second transfer tube; a third clamp that closes and opens the third transfer tube; and a fourth clamp that closes and opens the fourth transfer tube.

According to such a configuration, when the first clamp is opened, and the fourth clamp is closed, the light specific gravity blood component obtained by centrifugation of the first bag may be smoothly transferred to the second bag without being allowed to flow into the fifth bag. In addition, when the second clamp is opened, and the third clamp is closed, the heavy specific gravity blood component obtained by centrifugation of the first bag may be smoothly transferred to the third bag without being allowed to flow into the fourth bag. Further, when the second clamp is closed, and the third clamp is opened, the added solution in the fourth bag may be smoothly transferred to the first bag without being allowed to flow into the third bag. Furthermore, when the first clamp is closed, and the fourth clamp is opened, the waste liquid discharged from the first bag may be transferred to the fifth bag without being allowed to flow into the second bag.

According to the blood bag system, in the transfer completed state, the heavy specific gravity blood component may remain in the first bag, the light specific gravity blood component may be stored in the second bag, and the medium specific gravity blood component may be stored in the third bag, and the third transfer tube may be a tube for transferring the added solution from the fourth bag to the third bag.

According to such a configuration, it is possible to efficiently store a medium specific gravity blood component having a sufficiently low content rate of a light specific gravity blood component in the third bag.

The blood bag system may include: a fifth bag that stores a waste liquid containing the light specific gravity blood component and the added solution discharged from the third bag; and a fourth transfer tube for transferring the waste liquid discharged from the third bag to the fifth bag.

According to such a configuration, since the waste liquid discharged from the third bag is stored in the fifth bag, the waste liquid may be easily treated.

A blood treatment method according to the present invention includes: a centrifugation process of centrifuging whole blood or a blood component in a first bag into a light specific gravity blood component, a medium specific gravity blood component, and a heavy specific gravity blood component for each specific gravity; a first transfer process of transferring one of the light specific gravity blood component, the medium specific gravity blood component, and the heavy specific gravity blood component from the first bag to a second bag through a first transfer tube, and transferring the other one from the first bag to a third bag through a second transfer tube; and a second transfer process of transferring an added solution stored in a fourth bag to a bag accommodating the medium specific gravity blood component through a third transfer tube while a centrifugal force is applied to the bag after the first transfer process to discharge the light specific gravity blood component remaining in the medium specific gravity blood component from the bag, thereby obtaining a washed medium specific gravity blood component.

According to such a method, since the light specific gravity blood component remaining in the medium specific gravity blood component in the second transfer process may be discharged from the bag by the added solution, it is possible to obtain a washed medium specific gravity blood component. In this way, it is possible to more securely and efficiently obtain a medium specific gravity blood component having a sufficiently low content rate of a light specific gravity blood component.

According to the blood treatment method, in the first transfer process, the light specific gravity blood component may be transferred to the second bag, and the heavy specific gravity blood component may be transferred to the third bag, thereby leaving the medium specific gravity blood component in the first bag, and in the second transfer process, the added solution stored in the fourth bag may be transferred to the first bag through the third transfer tube.

According to such a method, it is possible to efficiently store a medium specific gravity blood component having a sufficiently low content rate of a light specific gravity blood component in the first bag.

According to the blood treatment method, in the second transfer process, the first bag may be disposed in a centrifugal force direction from the fourth bag.

According to such a method, it is possible to transfer the added solution in the fourth bag to the first bag using a centrifugal force.

According to the blood treatment method, in the second transfer process, the added solution in the fourth bag may be transferred to the first bag through the third transfer tube by pressing the fourth bag.

According to such a method, it is possible to more securely transfer the added solution in the fourth bag to the first bag.

The blood treatment method may include: a third transfer process of transferring a waste liquid containing the light specific gravity blood component and the added solution discharged from the first bag to a fifth bag through a fourth transfer tube after the second transfer process.

According to such a method, since the waste liquid discharged from the first bag is stored in the fifth bag, the waste liquid may be easily treated.

According to the blood treatment method, in the third transfer process, a part of the added solution in the first bag may be transferred to the fifth bag by pressing the first bag in a state in which the third transfer tube is closed.

According to such a method, a residual amount of the blood plasma in the first bag may be further reduced.

According to the blood treatment method, in the second transfer process, the added solution may be introduced to an outer diameter side of the first bag.

According to such a method, the light specific gravity blood component remaining in the first bag may be efficiently discharged from the first bag by the added solution.

The blood treatment method may include: a pooling process of collecting the washed medium specific gravity blood component in a plurality of bags in one pooling bag; and a white blood cell removal process of removing a white blood cell from the washed medium specific gravity blood component in the pooling bag.

According to such a method, the white blood cell may be removed, and the washed medium specific gravity blood component may be obtained.

Advantageous Effects of Invention

According to the invention, since a light specific gravity blood component remaining in a medium specific gravity blood component may be discharged from a bag using an added solution, it is possible to securely and efficiently obtain a medium specific gravity blood component having a sufficiently low content rate of a light specific gravity blood component.

DESCRIPTION OF EMBODIMENTS

Hereinafter, a blood bag system and a blood treatment method according to the invention will be described with reference to accompanying drawings using suitable embodiments.

First Embodiment

A blood bag system 10 according to a first embodiment of the invention is intended to obtain a washed buffy coat used to refine a washed platelet (platelet preparation) having a sufficiently low blood plasma content rate. Specifically, the blood bag system 10 is intended to centrifuge blood (whole blood) containing a plurality of blood components into three blood components corresponding to blood plasma, a buffy coat, and red cell concentrates, and add a platelet added solution (also referred to as a platelet cleaning solution or a platelet preservation solution) to the buffy coat to refine the washed buffy coat.

Figure 1:
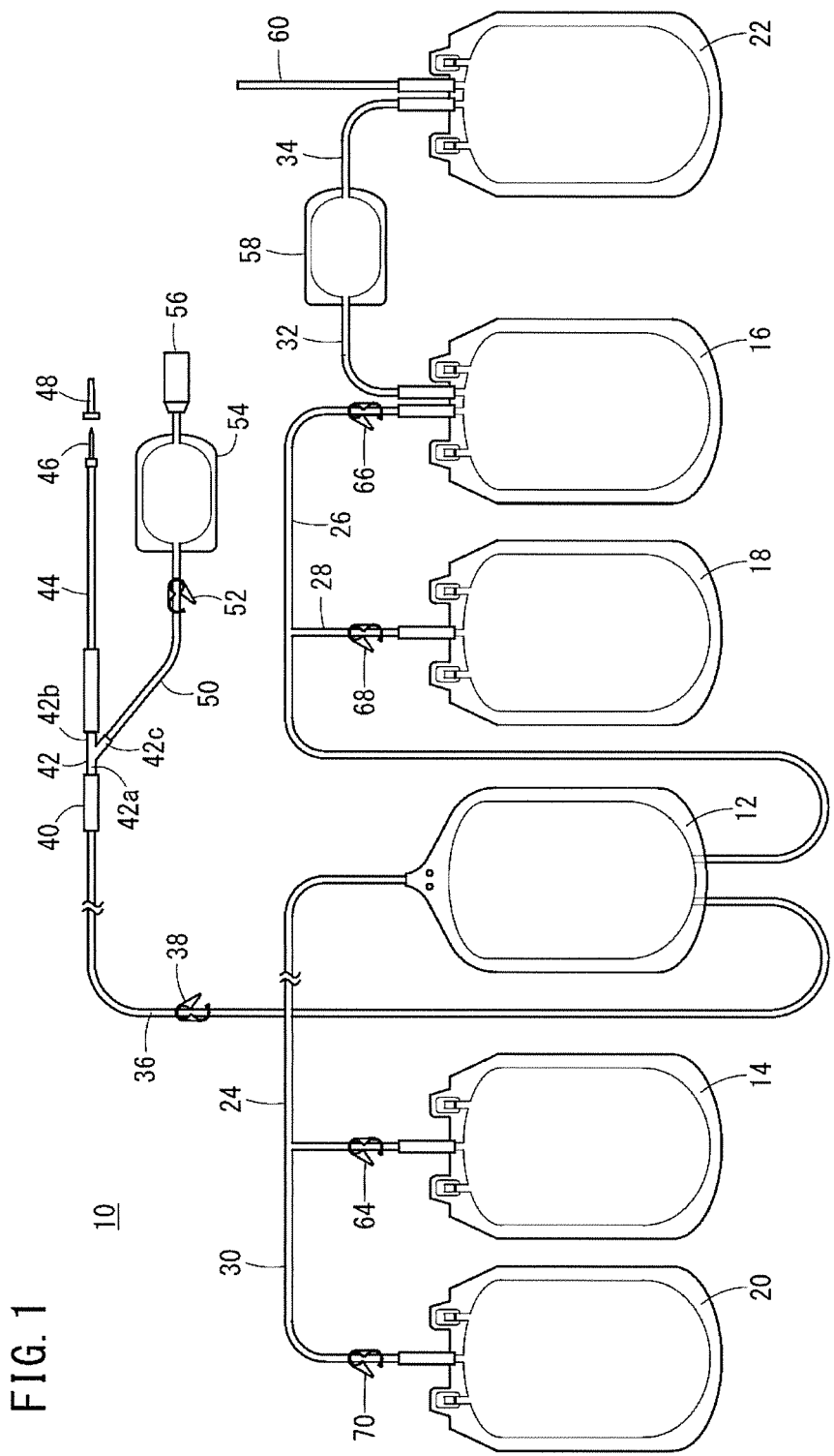
FIG. 1 is a schematic view illustrating an overall configuration of a blood bag system according to a first embodiment of the invention.

As illustrated in FIG. 1, the blood bag system 10 includes a plurality of bags (first to sixth bags 12, 14, 16, 18, 20, and 22) and a plurality of transfer tubes (first to sixth transfer tubes 24, 26, 28, 30, 32, and 34). For example, each of the first to sixth bags 12, 14, 16, 18, 20, and 22 is formed in a bag shape by stacking a sheet material having flexibility made of a soft resin such as polyvinyl chloride or polyolefin, and performing fusion bonding (thermal fusion bonding or high frequency fusion bonding) or adhesion in a seal portion at a periphery thereof. An initial flow blood bag 54 described below is similarly formed in a bag shape.

The first bag 12 is a bag for accommodating (storing) blood (whole blood) collected from a donor. Hereinafter, the first bag 12 may be referred to as a "blood collection bag 12". The blood collection bag 12 is used to store whole blood at the time of blood collection. However, as described below, after blood plasma obtained by centrifuging the whole blood is transferred to the second bag 14, and the red cell concentrates are transferred to the third bag 16, the blood collection bag 12 is used to store and preserve the washed buffy coat obtained by adding the platelet added solution to the buffy coat corresponding to a remaining blood component. That is, the blood collection bag 12 serves as both a whole blood accommodation bag and a washed buffy coat accommodation bag.

A blood preservation solution having a blood anticoagulant function is stored in the blood collection bag 12 in advance. Examples of the blood preservation solution include a blood preservation solution containing citric acid, phosphoric acid, glucose (citrate phosphate dextrose (CPD)), and the like. An amount of the blood preservation solution is set to an appropriate amount according to a scheduled blood collection amount.

In addition, one end of a blood collection tube 36 on a proximal end side is connected to a lower part of the blood collection bag 12. A clamp 38 for closing and opening a flow path of the blood collection tube 36 is provided in a midway portion of the blood collection tube 36. One end of a sealing member 40 is connected to the other end of the blood collection tube 36. The sealing member 40 may be configured such that a flow path is closed in initial state and opened by performing a breaking operation.

A first port 42a of a branch connector 42 is connected to the other end of the sealing member 40. One end of the blood collection tube 44 on a distal end side is connected to a second port 42b of the branch connector 42, and a blood collection needle 46 is connected to the other end of the blood collection tube 44. A cap 48 is attached to the blood collection needle 46 before use.

One end of a branch tube 50 is connected to a third port 42c of the branch connector 42. A clamp 52 for closing and opening a flow path of the branch tube 50 is provided at a midway portion of the branch tube 50. The initial flow blood bag 54 is connected to the other end of the branch tube 50. A sampling port 56 is connected to the initial flow blood bag 54. A direction and arrangement of the branch connector 42 is not limited to the configuration illustrated in FIG. 1, and may be appropriately changed.

The second bag 14 is connected to the blood collection bag 12 through the first transfer tube 24 and is a bag for accommodating (storing) and preserving blood plasma corresponding to a light specific gravity blood component obtained by centrifugation. Hereinafter, the second bag 14 may be referred to as a "blood plasma bag 14". The first transfer tube 24 is a tube for connecting an upper part of the blood collection bag 12 and an inlet of the blood plasma bag 14 and transferring the blood plasma from the blood collection bag 12 to the blood plasma bag 14.

The third bag 16 is connected to the blood collection bag 12 through the second transfer tube 26 and is a bag for accommodating (storing) and preserving red cell concentrates corresponding to a heavy specific gravity blood component obtained by centrifugation. Hereinafter, the third bag 16 may be referred to as a "first red blood cell bag 16". The second transfer tube 26 is a tube for connecting the lower part of the blood collection bag 12 and an inlet of the first red blood cell bag 16 and transferring the red cell concentrates from the blood collection bag 12 to the first red blood cell bag 16. The red cell concentrates stored and preserved in the first red blood cell bag 16 are red cell concentrates before removing a predetermined cell (white blood cell) (before filtration).

For example, an SAG-M (Saline Adenine Glucose Mannitol) liquid which is a mixed solution containing mannitol, glucose, adenine and sodium chloride is stored as a red blood cell preservation solution in the first red blood cell bag 16. Therefore, when the red cell concentrates obtained by centrifugation are transferred to the first red blood cell bag 16, a mixed liquid of the red cell concentrates before filtration and the red blood cell preservation solution (hereinafter referred to as "RC-SAGM") is stored in the first red blood cell bag 16.

The fourth bag 18 is connected to the first bag 12 through the third transfer tube 28 and the second transfer tube 26, and is a bag for accommodating (storing) and preserving the platelet added solution. Hereinafter, the fourth bag 18 may be referred to as an "added solution bag 18". The third transfer tube 28 is a tube for connecting an inlet of the added solution bag 18 and a midway portion of the second transfer tube 26 and transferring the platelet added solution to the blood collection bag 12 through the second transfer tube 26. The specific gravity of the platelet added solution is smaller than that of the buffy coat.

The fifth bag 20 is connected to the blood collection bag 12 through the fourth transfer tube 30 and the first transfer tube 24 and is a bag for accommodating a waste liquid (a mixed liquid of the blood plasma and the platelet added solution) generated when the washed buffy coat is refined. Hereinafter, the fifth bag 20 may be referred to as a "waste liquid bag 20". The fourth transfer tube 30 is a tube for connecting an inlet of the waste liquid bag 20 and a midway portion of the first transfer tube 24 and transferring the waste liquid in the blood collection bag 12 to the waste liquid bag 20 through the first transfer tube 24.

The sixth bag 22 is connected to the third bag 16 through the fifth transfer tube 32, a filter 58 and the sixth transfer tube 34, and is a bag for accommodating (storing) and preserving the red cell concentrates from which the white blood cell is removed (specifically obtained by removing the white blood cell from the RC-SAGM). Hereinafter, the sixth bag 22 may be referred to as a "second red blood cell bag 22".

The fifth transfer tube 32 is a tube for connecting the first red blood cell bag 16 and the filter 58 and transferring the red cell concentrates from the first red blood cell bag 16 to the filter 58. The filter 58 has a function of removing a predetermined cell, and, it is configured as a white blood cell removal filter in the present embodiment.

The sixth transfer tube 34 is a tube for connecting the filter 58 and the second red blood cell bag 22 and transferring the red cell concentrates from which the white blood cell is removed from the filter 58 to the second red blood cell bag 22. A sampling tube 60 for taking out a part of the red cell concentrates is connected to the second red blood cell bag 22.

Each tube in the blood bag system 10 is a transparent and flexible resin tube.

Figure 2:
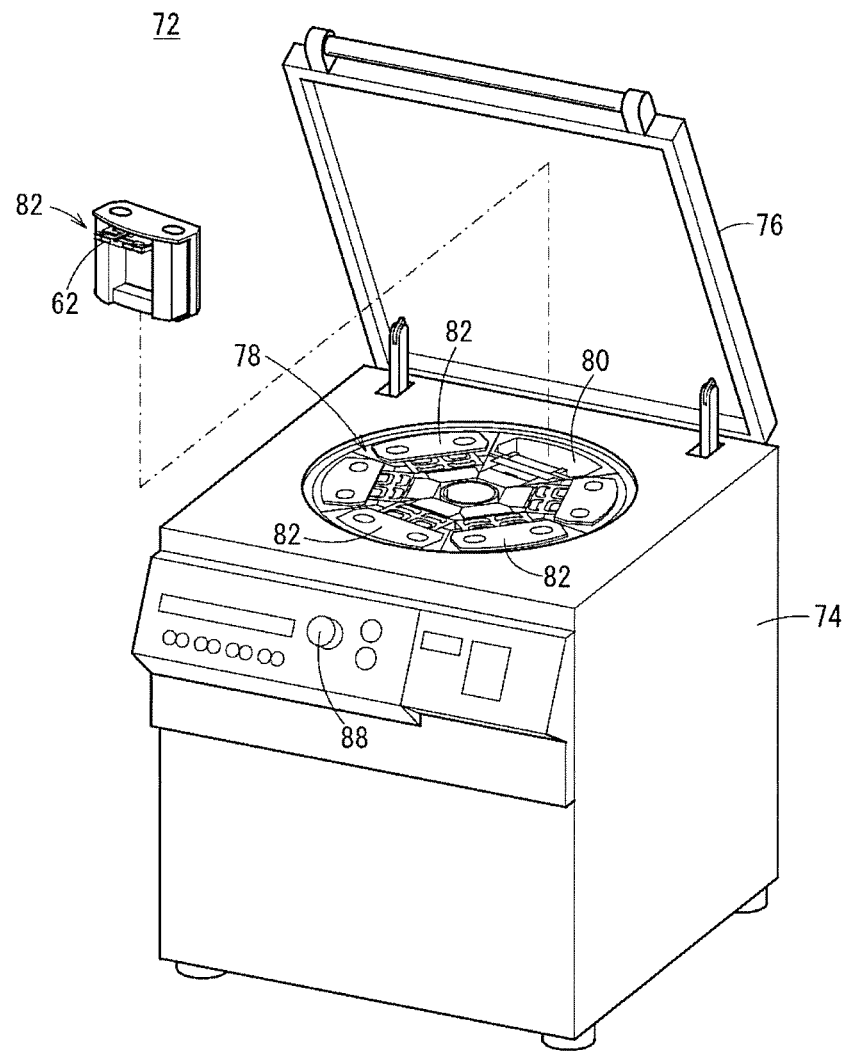
FIG. 2 is a perspective view of a centrifugation transfer device.

As illustrated in FIG. 2, the blood bag system 10 further includes a cassette 62. Although not illustrated in detail in the present embodiment, the cassette 62 is configured to hold the blood collection bag 12 and hold each part of the first to fourth transfer tubes 24, 26, 28, and 30.

Figure 3:
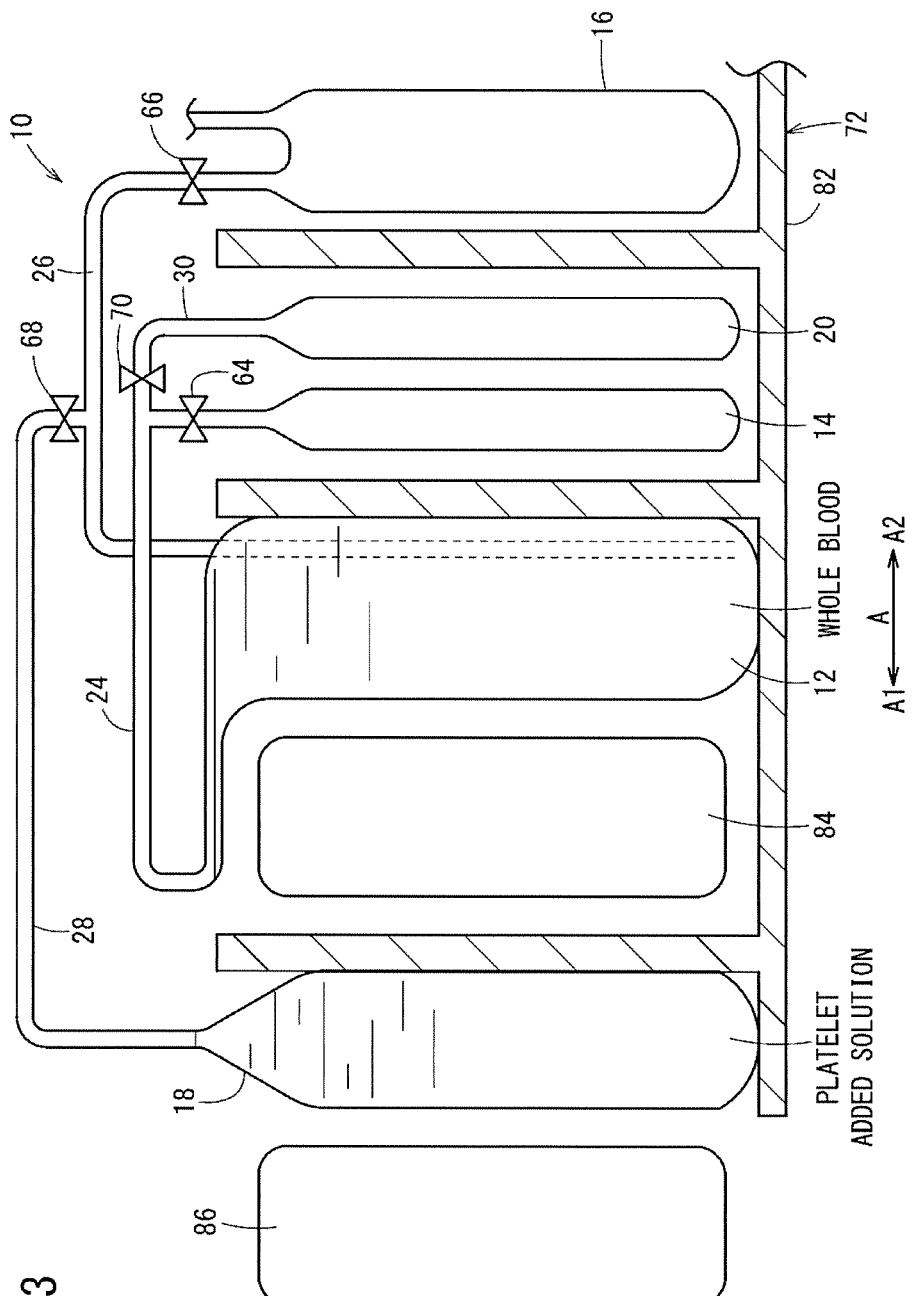
FIG. 3 is a schematic view illustrating a state of the blood bag system before a centrifugation process.

As illustrated in FIGS. 1 and 3, the blood bag system 10 includes first to fourth clamps 64, 66, 68, and 70 provided in the cassette 62. The first clamp 64 closes and opens a flow path of the first transfer tube 24 on a blood plasma bag 14 side of a connecting portion connected to the fourth transfer tube 30. The second clamp 66 closes and opens a flow path of the second transfer tube 26 on a first red blood cell bag 16 side of a connecting portion connected to the third transfer tube 28. The third clamp 68 closes and opens a flow path of the third transfer tube 28. The fourth clamp 70 closes and opens a flow path of the fourth transfer tube 30. Each of the first to fourth clamps 64, 66, 68, and 70 is configured to be opened and closed by clamp drive means (not illustrated).

For example, the blood bag system 10 configured as described above is attached to a centrifugation transfer device 72 illustrated in FIG. 2 and used. As illustrated in FIG. 2, the centrifugation transfer device 72 has a box shape, and includes a main device body 74, an openable lid 76 on an upper surface, a centrifugal drum 78 on an inside, six unit insertion holes 80 provided at equal angle intervals (60°) in the centrifugal drum 78, six insert units 82 inserted into the respective unit insertion holes 80, and six first pushers 84 and six second pushers 86 which are provided in a center portion and capable of advancing and retracting in a rotation radial direction with respect to the respective insert units 82 (see FIG. 3). The centrifugation transfer device 72 operates based on an operation of an operation unit 88 provided on a front surface, and is controlled by a microcomputer (not illustrated).

In a state in which the insert units 82 are inserted into the unit insertion holes 80, a direction of an arrow A of FIG. 3 corresponds to a radial direction of the centrifugal drum 78. In particular, a direction of an arrow A1 corresponds to a radially inward direction of the centrifugal drum 78, and a direction of an arrow A2 corresponds to a radially outward direction of the centrifugal drum 78 (a centrifugal force direction at the time of centrifugation). A plurality of chambers (not illustrated) is formed in the insert units 82 to hold the blood collection bag 12, the blood plasma bag 14, the first red blood cell bag 16, the added solution bag 18, the waste liquid bag 20, and the second red blood cell bag 22.

As illustrated in FIG. 3, in the present embodiment, in the state in which the insert units 82 are inserted into the unit insertion holes 80, the blood collection bag 12 is located in the direction of the arrow A2 from the added solution bag 18, and the blood plasma bag 14, the waste liquid bag 20 and the first red blood cell bag 16 are located in the direction of the arrow A2 from the blood collection bag 12. However, arrangement of the blood collection bag 12, the blood plasma bag 14, the first red blood cell bag 16, the added solution bag 18 and the waste liquid bag 20 with respect to the insert units 82 is not limited to an example of FIG. 3 and may be freely changed. Further, the first pusher 84 may be provided to be able to press the blood collection bag 12 in a rotation direction (circumferential direction) of the insert unit 82, and the second pusher 86 may be provided to be able to press the added solution bag 18 in the rotation direction (circumferential direction) of the insert unit 82. In other words, a scheme of arranging and driving the first pusher 84 and the second pusher 86 is not limited as long as the pushers may press the bags.

Basically, the blood bag system 10 according to the present embodiment is configured as described above. Next, the blood treatment method (a method of refining the washed platelet) of the present embodiment will be described. In the present embodiment, a washed buffy coat refinement process (primary centrifugation process), a pooling process, and a white blood cell removal process (secondary centrifugation process) are successively performed.

A blood collection process, a mounting process, a centrifugation process, a first transfer process, a second transfer process and a third transfer process are performed in the washed buffy coat refinement process. In the blood collection process, prior to collection of blood into the blood collection bag 12, an initial flow of blood (initial collected blood flow) from the donor is stored in the initial flow blood bag 54 by a predetermined amount. In this case, while the sealing member 40 is in a closed state (initial state), the clamp 52 is brought into an open state. In this way, while inflow of the initial collected blood flow into the blood collection tube 36 side, that is, the blood collection bag 12 side is inhibited, the initial collected blood flow may be introduced to the initial flow blood bag 54 through the blood collection tube 36, the branch connector 42, and the branch tube 50.

Subsequently, a blood sampling tube (not illustrated) is attached to the sampling port, so that the initial collected blood flow is collected in the blood sampling tube. The collected initial collected blood flow is used as blood for examination. Depending on the use, a part from the branch connector 42 to the sampling port may be omitted.

When collection of the initial collected blood flow is completed, the branch tube 50 is closed by the clamp 52, and the flow path of the blood collection tube 36 is opened by performing a breaking operation on the sealing member 40. In this instance, the clamp 38 is in an open state. Then, the blood from the donor flows into the blood collection bag 12 through the blood collection tube 36 in order. Before collection of blood in the blood collection bag 12 starts, it is preferable that the blood collection bag 12 and the first to fourth transfer tubes 24, 26, 28, and 30 are held by the cassette 62, and the first to fourth clamps 64, 66, 68, and 70 are closed by the clamp drive means (not illustrated) to close the respective flow paths of the first to fourth transfer tubes 24, 26, 28, and 30.

When a predetermined amount of blood is collected and stored in the blood collection bag 12, the blood collection tube 36 is closed by the clamp 38 so that the blood in the blood collection bag 12 does not flow out. Then, after the blood collection tube 36 is welded and sealed by a tube sealer and the like, the blood collection tube 36 is cut at a sealed portion. In description of subsequent processes, a portion of the whole blood bag system 10 illustrated in FIG. 1 on the blood collection bag 12 side of a cut portion of the blood collection tube 36 is also referred to as the "blood bag system 10".

In the mounting process, the blood bag system 10 is attached to the centrifugation transfer device 72 (see FIG. 2). In attachment of the blood bag system 10 to the centrifugation transfer device 72, the cassette 62 holding the blood collection bag 12 and the first to fourth transfer tubes 24, 26, 28, and 30 is attached to the insert unit 82. In this way, the blood collection bag 12 suspended and supported by the cassette 62 is in a state of being held in a chamber (not illustrated) of the insert unit 82. In addition, the blood plasma bag 14, the first red blood cell bag 16, the added solution bag 18, the waste liquid bag 20, the filter 58 and the second red blood cell bag 22 are held in a chamber (not illustrated) of the insert unit 82.

Subsequently, the insert unit 82 held in the blood bag system 10 is inserted into the unit insertion hole 80 of the centrifugation transfer device 72. Basically, the six insert units 82 are attached to the centrifugation transfer device 72. However, five or fewer (preferably three or two at equal angle intervals) insert units 82 may be used when the insert units 82 are balanced.

Subsequently, after the lid 76 of the centrifugation transfer device 72 is closed, the centrifugation process, the first transfer process, the second transfer process, and the third transfer process are automatically performed by operating the operation unit 88. Here, FIG. 3 is a schematic view illustrating a state of the blood bag system 10 before performing the centrifugation process (before applying a centrifugal force). The first to fourth clamps 64, 66, 68, and 70 are closed in advance, whereby the respective flow paths of the first to fourth transfer tubes 24, 26, 28, and 30 are closed.

Figure 4:
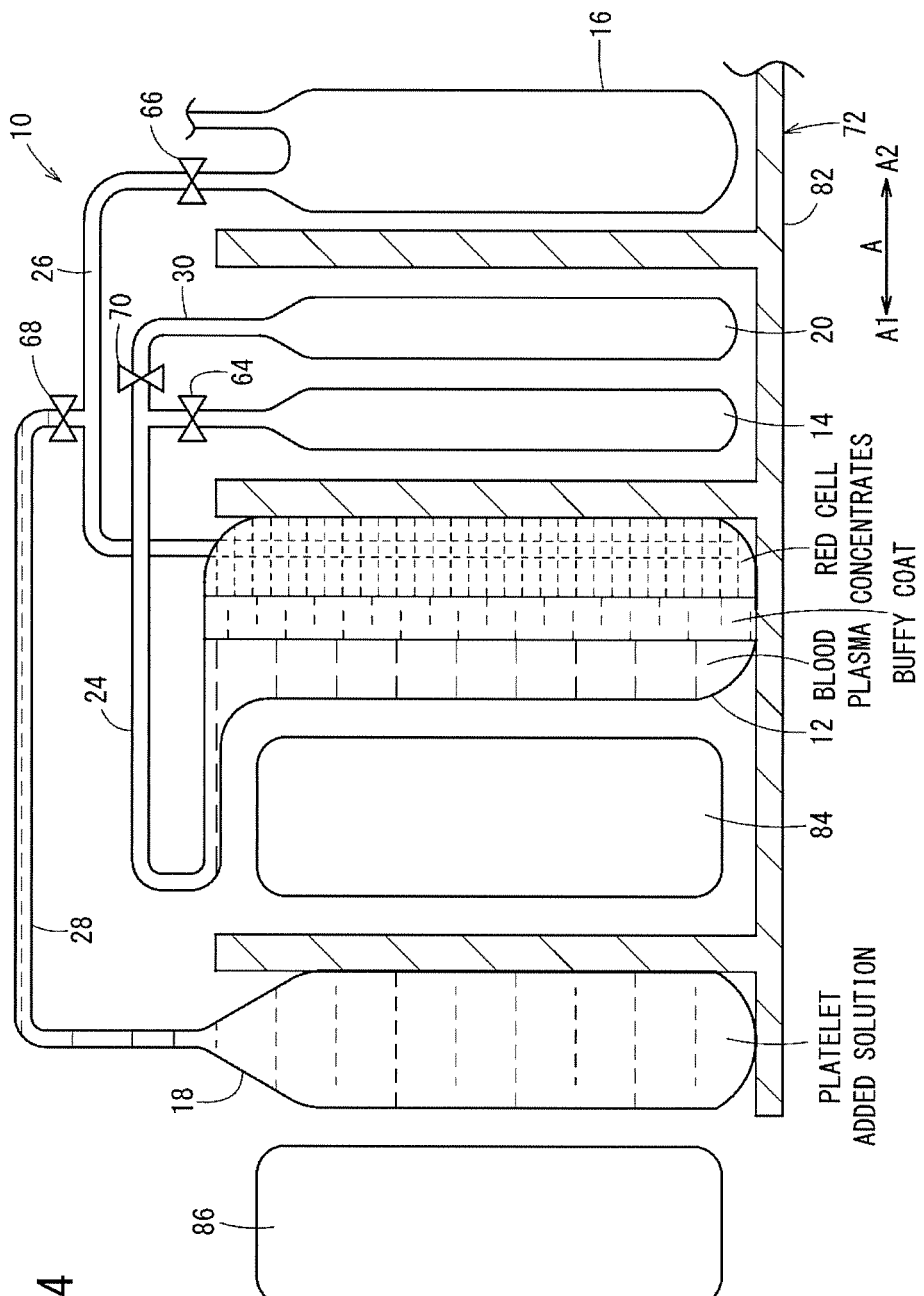
FIG. 4 is a schematic view illustrating a state of the blood bag system after the centrifugation process and before a first transfer process.

As illustrated in FIG. 4, in the centrifugation process, the centrifugation transfer device 72 rotates the centrifugal drum 78. Then, in response to the whole blood stored in the blood collection bag 12 receiving a centrifugal force, the red cell concentrates corresponding do a heavy specific gravity blood component move in the radially outward direction (the direction of the arrow A2), the blood plasma corresponding to a light specific gravity blood component moves in the radially inward direction (the direction of the arrow A1), and the buffy coat corresponding to a medium specific gravity blood component moves to an intermediate position therebetween, thereby separating the blood into three layers.

Subsequently, the centrifugation transfer device 72 proceeds to the first transfer process. In the first transfer process, while a centrifugal force is applied to the blood collection bag 12 by maintaining rotation of the centrifugal drum 78, the first clamp 64 and the second clamp 66 are opened by operating the clamp drive means (not illustrated). In this way, each of the flow paths of the first transfer tube 24 and the second transfer tube 26 is in an open state.

Figure 5:
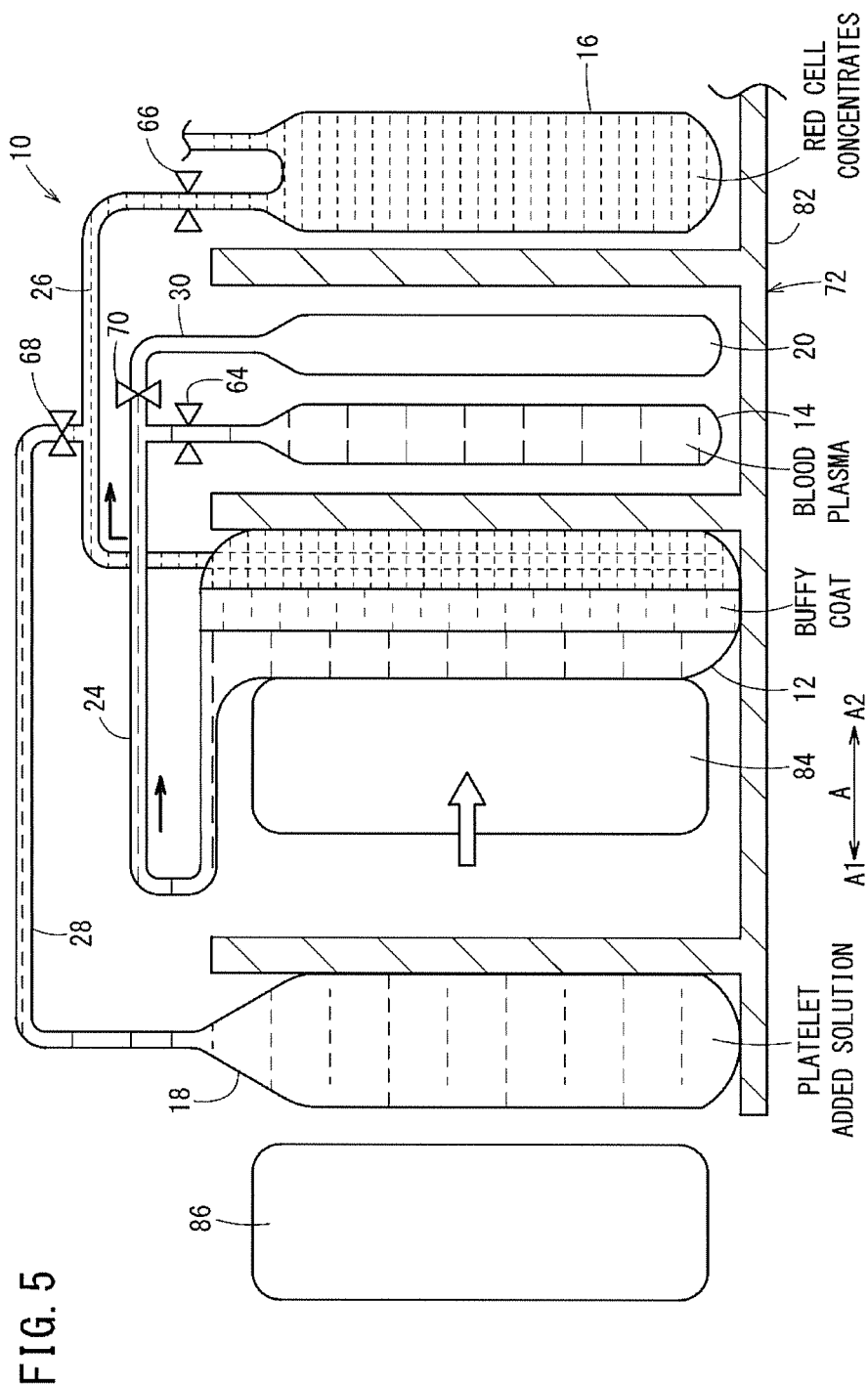
FIG. 5 is a schematic view illustrating a state of the blood bag system during the first transfer process.

Then, as illustrated in FIG. 5, the first pusher 84 is shifted in the centrifugal force direction, that is, in the radially outward direction (the direction of the arrow A2) to press the blood collection bag 12. The blood collection bag 12 is interposed between the first pusher 84 and a wall, and thus the volume thereof is reduced. In this instance, since the first transfer tube 24 is oriented toward an inner diameter side, blood plasma located on an innermost diameter side flows out from the blood collection bag 12 to the first transfer tube 24 and flows into the blood plasma bag 14 through the first transfer tube 24.

Meanwhile, since the second transfer tube 26 is connected to an outer diameter side of the blood collection bag 12, the red cell concentrates located on an outermost diameter side flow out from the blood collection bag 12 to the second transfer tube 26 and flow into the first red blood cell bag 16 through the second transfer tube 26.

When an optical sensor (not illustrated) detects that the red cell concentrates are transferred from the second transfer tube 26, and a separation surface of the red cell concentrates and the buffy coat arrives at a predetermined position, the flow path of the second transfer tube 26 is closed by closing the second clamp 66.

In addition, when the microcomputer (not illustrated) detects that the blood plasma is transferred from the first transfer tube 24, and the first pusher 84 reaches a predetermined position, the flow path of the first transfer tube 24 is closed by closing the first clamp 64. The first pusher 84 is stopped in a step in which both the first clamp 64 and the second clamp 66 are closed.

Figure 6:
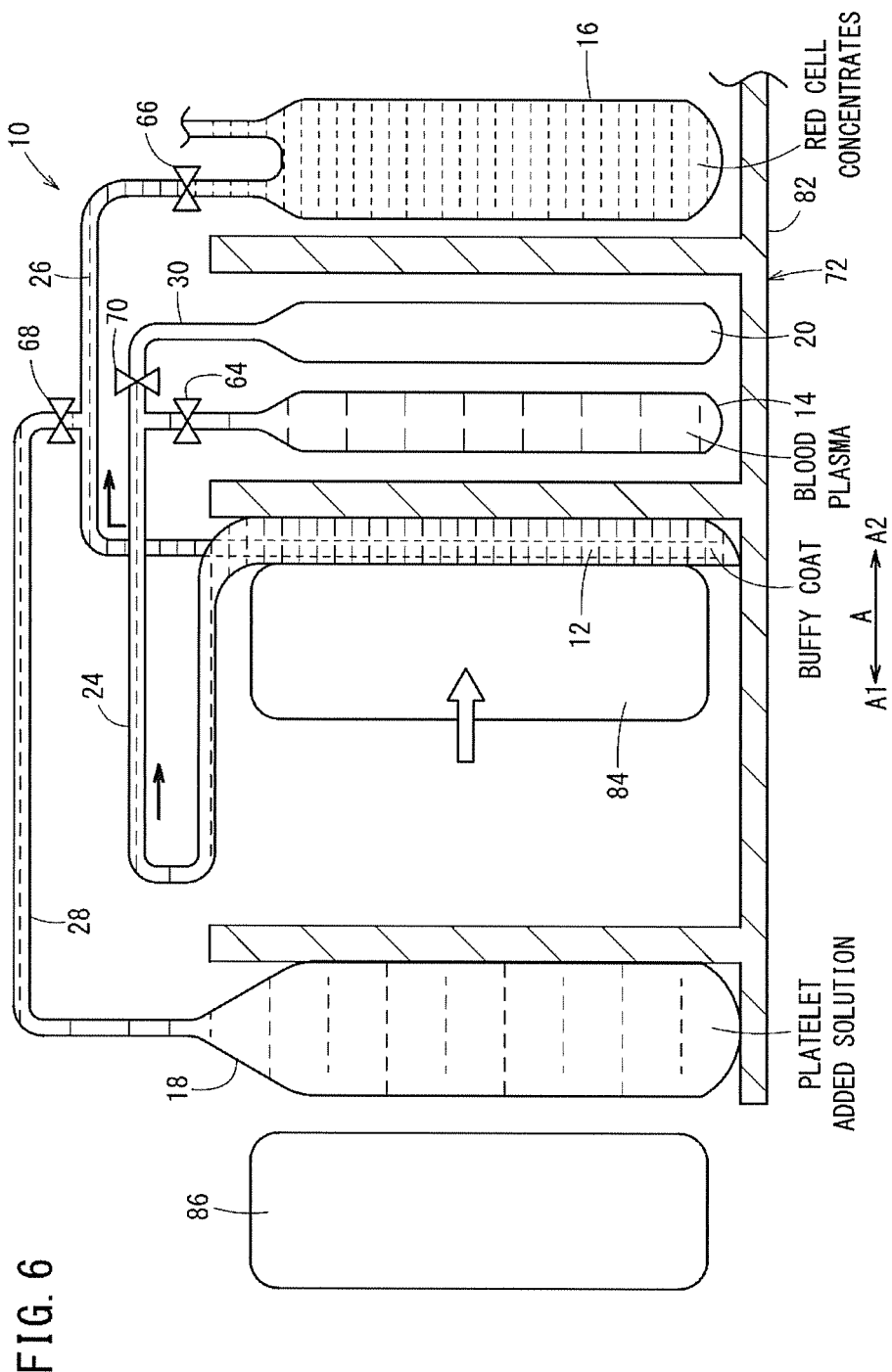
FIG. 6 is a schematic view illustrating a state of the blood bag system at the time when the first transfer process is completed.

As illustrated in FIG. 6, the buffy coat is stored in the blood collection bag 12 at the time when the first transfer process is completed.

Subsequently, the centrifugation transfer device 72 proceeds to the second transfer process. In the second transfer process, while a centrifugal force is applied to the added solution bag 18 by maintaining rotation of the centrifugal drum 78, the third clamp 68 and the fourth clamp 70 are opened by operating the clamp drive means (not illustrated). In this way, each of the flow paths of the third transfer tube 28 and the fourth transfer tube 30 is in an open state.

Figure 7:
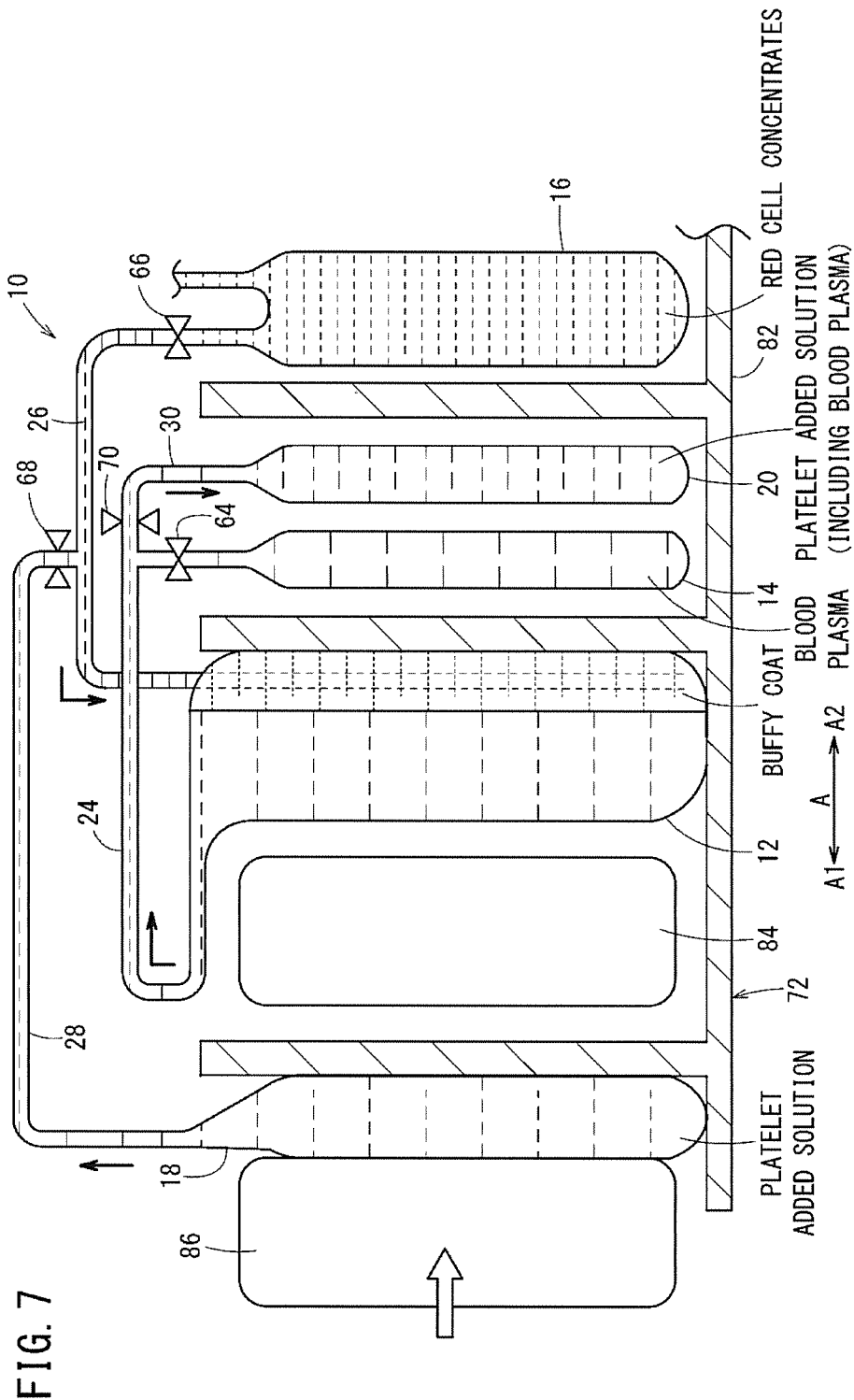
FIG. 7 is a schematic view illustrating a state of the blood bag system during a second transfer process.

Then, as illustrated in FIG. 7, the second pusher 86 is shifted in the centrifugal force direction, that is, in the radially outward direction (the direction of the arrow A2) to press the added solution bag 18. The added solution bag 18 is interposed between the second pusher 86 and a wall, and thus the volume thereof is reduced. In this way, the platelet added solution flows out from the added solution bag 18 to the third transfer tube 28 and flows into the blood collection bag 12 through the third transfer tube 28 and the second transfer tube 26. In this instance, since the second clamp 66 is closed, the platelet added solution is not mixed with the red cell concentrates stored in the first red blood cell bag 16.

In addition, since the specific gravity of the platelet added solution is smaller than that of the buffy coat, when the platelet added solution flows into an outer diameter side of the blood collection bag 12 from the second transfer tube 26, blood plasma in the buffy coat is pressed to an inner diameter side (in the direction of the arrow A1) by the platelet added solution to flow out from the blood collection bag 12 to the first transfer tube 24 and flow into the waste liquid bag 20 through the first transfer tube 24 and the fourth transfer tube 30. In this instance, since the first clamp 64 is closed, the platelet added solution is not mixed with the blood plasma stored in the blood plasma bag 14.

When the microcomputer (not illustrated) detects that the platelet added solution is transferred from the added solution bag 18, and the second pusher 86 arrives at a predetermined position, the flow path of the third transfer tube 28 is closed by closing the third clamp 68, and the second pusher 86 is stopped. The fourth clamp 70 is kept in the open state.

Figure 8:
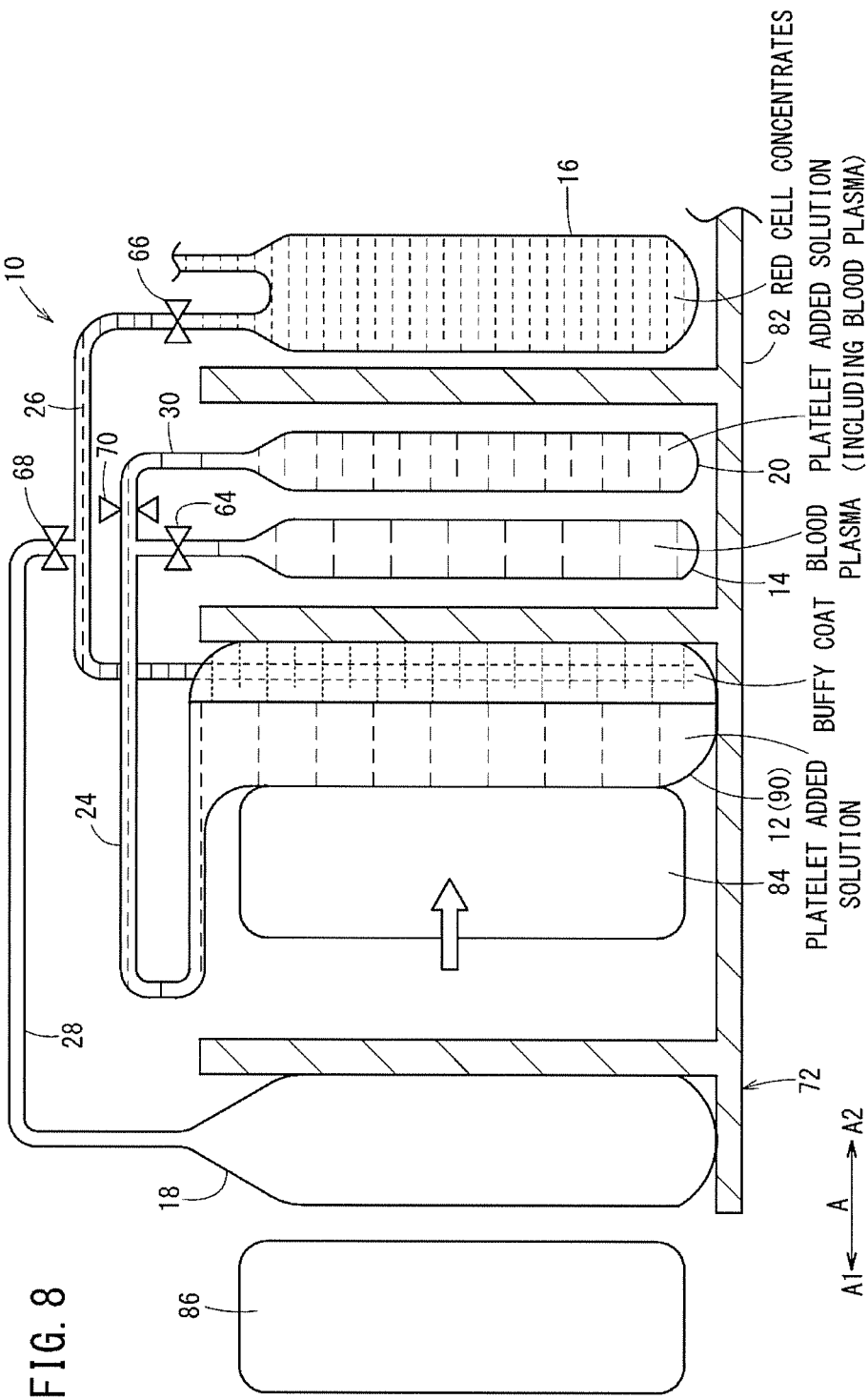
FIG. 8 is a schematic view illustrating a state of the blood bag system during a third transfer process.

Thereafter, the centrifugation transfer device 72 proceeds to the third transfer process. In the third transfer process, while a centrifugal force is applied to the blood collection bag 12 by maintaining rotation of the centrifugal drum 78, the blood collection bag 12 is pressed by shifting the first pusher 84 in the centrifugal force direction as illustrated in FIG. 8. The blood collection bag 12 is interposed between the first pusher 84 and a wall, and thus the volume thereof is reduced. In this way, an extra platelet added solution in the blood collection bag 12 flows into the waste liquid bag 20 from the blood collection bag 12 through the first transfer tube 24.

When the microcomputer (not illustrated) detects that the first pusher 84 arrives at a predetermined position, the flow path of the fourth transfer tube 30 is closed by closing the fourth clamp 70, and the first pusher 84 is stopped.

When the third transfer process is completed, the blood bag system 10 is removed from the insert unit 82. Further, each bag is cut off by welding and sealing each of the first to fourth transfer tubes 24, 26, 28, and 30 in the blood bag system 10 using a tube sealer and the like, and then cutting each of the first to fourth transfer tubes 24, 26, 28, and 30. Thereafter, red cell concentrates temporarily stored in the first red blood cell bag 16 are passed through the filter 58 to remove a white blood cell. The red cell concentrates from which the white blood cell is removed are stored and preserved in the second red blood cell bag 22.

In description below, the blood collection bag 12 (the first bag 12) accommodating the washed buffy coat obtained by the washed buffy coat refinement process may be referred to as a "cleaning BC bag 90".

Figure 9:
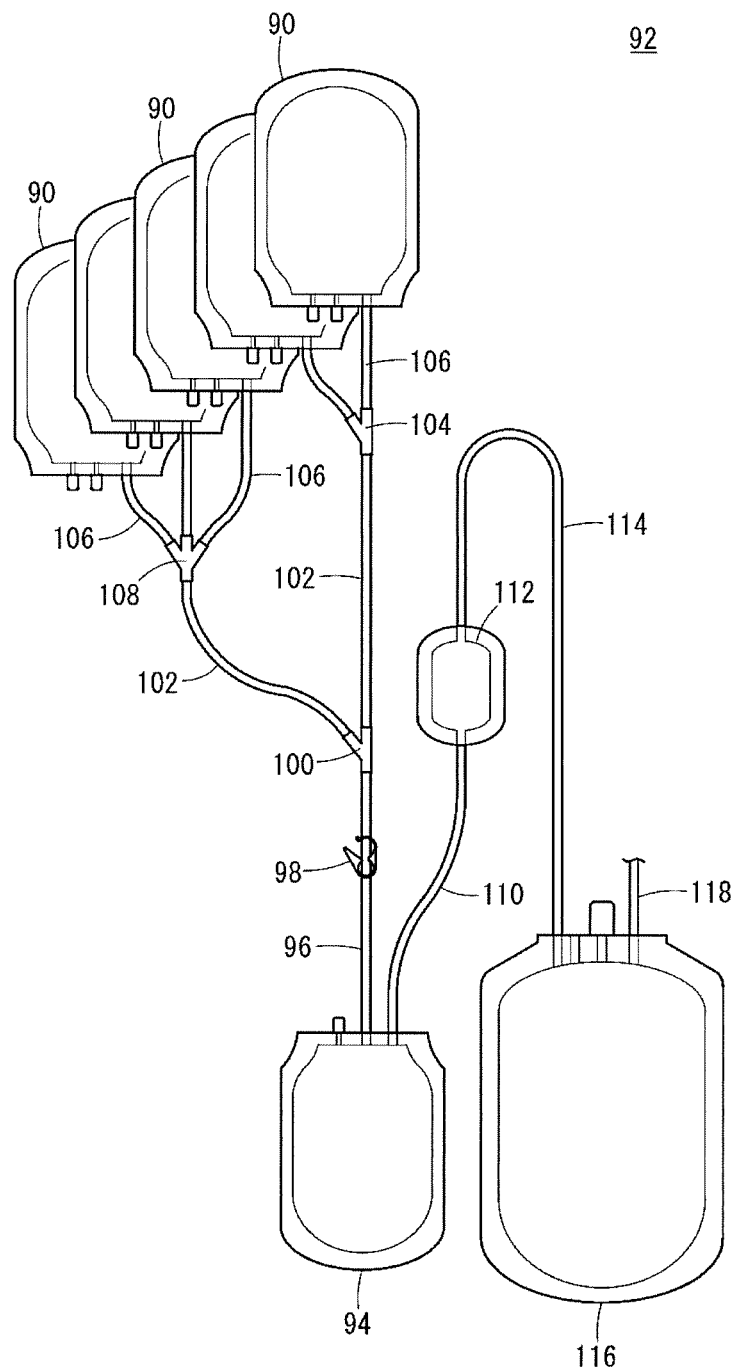
FIG. 9 is a schematic view for description of a pooling process.

Subsequently, in the pooling process, first, a platelet bag system 92 is configured by connecting a plurality of (five in FIG. 9) cleaning BC bags 90 to a tube. As illustrated in FIG. 9, the platelet bag system 92 includes the plurality of cleaning BC bags 90 obtained in the washed buffy coat refinement process and a pooling bag 94 in which buffy coats in the cleaning BC bags 90 are collected.

One end of an introduction tube 96 is connected to an upper portion of the pooling bag 94. The introduction tube 96 is provided with a clamp 98 that closes and opens a flow path of the introduction tube 96. One ends of two first branch tubes 102 are connected to the other end of the introduction tube 96 through a first branch connector 100. One ends of two second branch tubes 106 are connected to the other end of one first branch tube 102 through a second branch connector 104, and one ends of three second branch tubes 106 are connected to the other end of the other first branch tube 102 through a third branch connector 108. The cleaning BC bags 90 are connected to the other ends of the respective second branch tubes 106.

In addition, one end of a first connection tube 110 is connected to the upper portion of the pooling bag 94. The other end of the first connection tube 110 is connected to a filter 112, and one end of a second connection tube 114 is connected to the filter 112. The other end of the second connection tube 114 is connected to a washed platelet bag 116. A sampling port 118 is connected to the washed platelet bag 116. Each bag of the platelet bag system 92 is configured similarly to the bag of the above-described blood bag system 10, and each tube of the platelet bag system 92 is configured similarly to the tube of the above-described blood bag system 10. The filter 112 is configured similarly to the filter 58 described above.

In the pooling process, the pooling bag 94 is disposed vertically below the plurality of cleaning BC bags 90 connected in parallel, and the clamp 98 is opened, thereby collecting the washed buffy coats in the respective cleaning BC bags 90 in the one pooling bag 94 through the second branch tubes 106, the first branch tubes 102, and the introduction tube 96 by action of gravity. Thereafter, the introduction tube 96 is welded and sealed by a sealer and the like, and then the introduction tube 96 is cut at a sealed portion. In description of subsequent processes, a portion of the whole platelet bag system 92 illustrated in FIG. 9 on the pooling bag 94 side of a cut portion of the introduction tube 96 is also referred to as the "platelet bag system 92".

Figure 10:
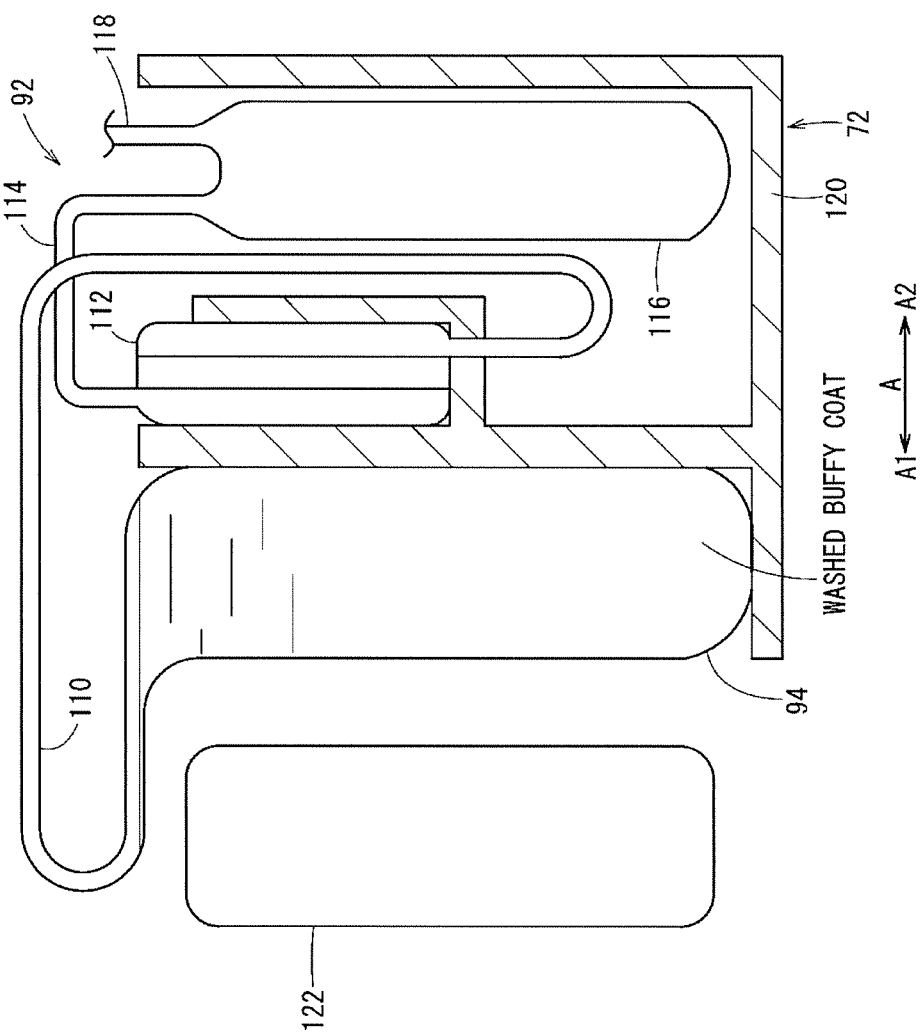
FIG. 10 is a schematic view illustrating a state before centrifugation of a washed buffy coat in a pooling bag attached to the centrifugation transfer device.

Subsequently, in the white blood cell removal process, as illustrated in FIG. 10, the pooling bag 94 of the platelet bag system 92 is attached to a cassette (not illustrated), and the cassette is attached to the insert unit 120 of the centrifugation transfer device 72. In this instance, the filter 112 is located in the radially outward direction (the direction of the arrow A2) of the pooling bag 94, and the washed platelet bag 116 is located in the radially outward direction (the direction of the arrow A2) of the filter 112. The insert unit 120 is insertable into the unit insertion hole 80 (see FIG. 2).

Figure 11:
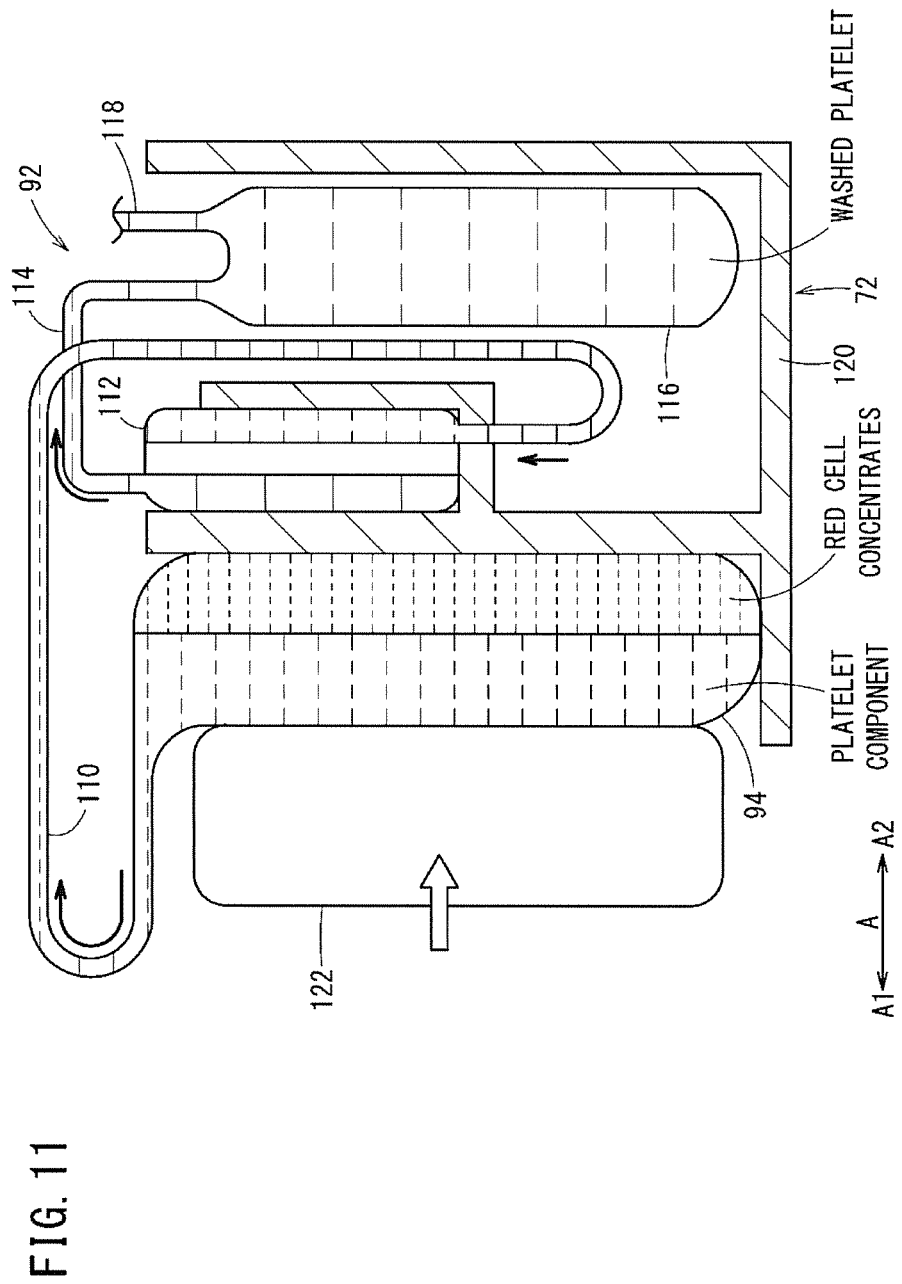
FIG. 11 is a schematic view illustrating a state of transferring a washed platelet, which is obtained by removing a white blood cell from a platelet component obtained by centrifugation of the washed buffy coat, to a washed platelet bag.

Thereafter, the centrifugation transfer device 72 rotates the centrifugal drum 78. Then, as illustrated in FIG. 11, the washed buffy coat stored in the pooling bag 94 receives a centrifugal force, so that the red cell concentrates move in the radially outward direction (the direction of the arrow A2), a platelet component moves in the radially inward direction (the direction of the arrow A1), and the red cell concentrates are separated into two layers.

Subsequently, while a centrifugal force is applied to the pooling bag 94 by maintaining rotation of the centrifugal drum 78, the pusher 122 is shifted in the centrifugal force direction, that is, the radially outward direction (the direction of the arrow A2) to press the pooling bag 94. The pooling bag 94 is interposed between the pusher 122 and a wall, and thus the volume thereof is reduced. In this instance, since the first connection tube 110 is oriented toward an inner diameter side, a platelet component located on an inner diameter side flows out from the pooling bag 94 to the first connection tube 110 and flows into the filter 112 through the first connection tube 110.

Then, a white blood cell is removed by passing the platelet component through the filter 112. The washed platelet corresponding to the platelet component from which the white blood cell is removed is stored and preserved in the washed platelet bag 116 through the second connection tube 114.

According to the present embodiment, in a transfer completed state in which the blood plasma and the red cell concentrates obtained by centrifuging the whole blood (content liquid) in the blood collection bag 12 are transferred to the blood plasma bag 14 and the first red blood cell bag 16, respectively, the platelet added solution in the added solution bag 18 is transferred to an outer diameter side of the blood collection bag 12 on which a centrifugal force acts. In this way, since the blood plasma remaining in the buffy coat may be pushed out (discharged) from the blood collection bag 12 by the platelet added solution, the washed buffy coat (washed medium specific gravity blood component) may be obtained. Therefore, it is possible to securely and efficiently obtain the washed buffy coat having a sufficiently low content rate of blood plasma in the blood collection bag 12. Since the washed platelet is refined using such a washed buffy coat, it is possible to securely and efficiently obtain the washed platelet having a sufficiently low blood plasma content rate.

In addition, since the waste liquid containing the blood plasma and the platelet added solution discharged from the blood collection bag 12 to the fourth transfer tube 30 is stored in the waste liquid bag 20, the waste liquid may be easily treated.

Further, the third transfer tube 28 connects the second transfer tube 26 and the added solution bag 18 to each other, and the fourth transfer tube 30 connects the first transfer tube 24 and the waste liquid bag 20 to each other. Therefore, it is possible to simplify configurations of the blood collection bag 12 and the tube.

In the present embodiment, since the waste liquid is transferred from the blood collection bag 12 to the waste liquid bag 20 in a state in which the first clamp 64 is opened and the fourth clamp 70 is closed, the waste liquid does not flow into the blood plasma bag 14.

In addition, since the red cell concentrates are transferred from the blood collection bag 12 to the first red blood cell bag 16 in a state in which the second clamp 66 is opened and the third clamp 68 is closed, the red cell concentrates do not flow into the added solution bag 18.

Further, since the platelet added solution is transferred from the added solution bag 18 to the blood collection bag 12 in a state in which the second clamp 66 is closed and the third clamp 68 is opened, the platelet added solution does not flow into the first red blood cell bag 16.

Furthermore, since the waste liquid is transferred from the blood collection bag 12 to the waste liquid bag 20 by closing the first clamp 64 and opening the fourth clamp 70, the waste liquid does not flow into the blood plasma bag 14.

According to the present embodiment, since the blood collection bag 12 is disposed in a centrifugal direction from the added solution bag 18 in the second transfer process, the platelet added solution may be transferred to the blood collection bag 12 by a centrifugal force.

In addition, since the added solution bag 18 is pressed by the second pusher 86 in the second transfer process, the platelet added solution may be more securely transferred to the blood collection bag 12.

Further, since a part of the platelet added solution in the blood collection bag 12 is transferred to the waste liquid bag 20 in a state in which the third transfer tube 28 is closed by the third clamp 68 in the third transfer process, a residual amount of the blood plasma in the blood collection bag 12 (the cleaning BC bag 90) may be further reduced.

Furthermore, since the platelet added solution is introduced to an outer diameter side of the blood collection bag 12 in the second transfer process, the blood plasma remaining in the blood collection bag 12 may be efficiently pushed out (discharged) from the blood collection bag 12 by the platelet added solution.

The present embodiment is not limited to the above-described configuration and method. For example, in the second transfer process, the platelet added solution may be transferred to the blood collection bag 12 only by a centrifugal force without pressing the added solution bag 18 by the second pusher 86.

Second Embodiment

Next, a description will be given of a blood bag system 10A and a blood treatment method according to a second embodiment of the invention. In the blood bag system 10A according to the present embodiment, the same reference symbol will be assigned to the same component as that in the blood bag system 10 according to the first embodiment described above, and a detailed description thereof will be omitted.

Figure 12:
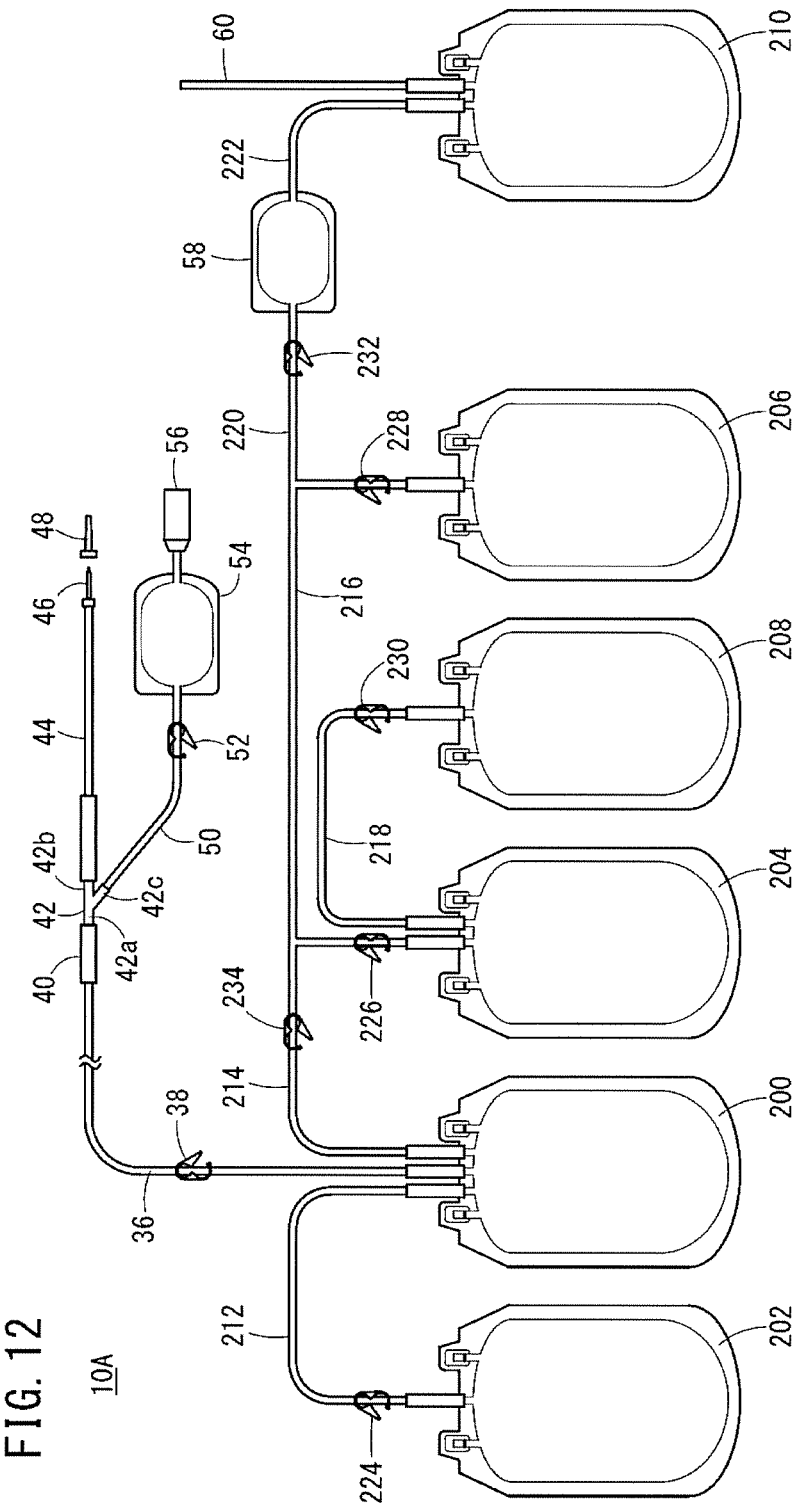
FIG. 12 is a schematic view illustrating an overall configuration of a blood bag system according to a second embodiment of the invention.

As illustrated in FIG. 12, the blood bag system 10A includes a plurality of bags (first to sixth bags 200, 202, 204, 206, 208, and 210) and a plurality of transfer tubes (first to sixth transfer tubes 212, 214, 216, 218, 220, and 222). For example, each of the first to sixth bags 200, 202, 204, 206, 208, and 210 is formed in a bag shape by stacking a sheet material having flexibility made of a soft resin such as polyvinyl chloride or polyolefin, and performing fusion bonding (thermal fusion bonding or high frequency fusion bonding) or adhesion in a seal portion at a periphery thereof.

The first bag 200 is a bag for accommodating (storing) blood (whole blood) collected from the donor. Hereinafter, the first bag 200 may be referred to as a "blood collection bag 200". As will be described below, after blood plasma obtained by centrifuging whole blood is transferred to the second bag 202, and a buffy coat is transferred to the third bag 204, red cell concentrates corresponding to remaining blood components are left in the blood collection bag 200. The same blood preservation solution as that in the above-described blood collection bag 200 is stored in the blood collection bag 200. One end of a blood collection tube 36 on a proximal end side is connected to an upper portion of the blood collection bag 200.

The second bag 202 is connected to the blood collection bag 200 through the first transfer tube 212, and is a bag for accommodating (storing) and preserving blood plasma corresponding to a light specific gravity blood component obtained by centrifugation. Hereinafter, the second bag 202 may be referred to as a "blood plasma bag 202". The first transfer tube 212 is a tube for connecting the upper portion of the blood collection bag 200 to an inlet of the blood plasma bag 202 and transferring the blood plasma from the blood collection bag 200 to the blood plasma bag 202.

The third bag 204 is connected to the blood collection bag 200 through the second transfer tube 214, and is a bag for accommodating (storing) and preserving a buffy coat corresponding to a medium specific gravity blood component obtained by centrifugation. Hereinafter, the third bag 204 may be referred to as a "buffy coat bag 204". The second transfer tube 214 is a tube for connecting the upper portion of the blood collection bag 200 to an inlet of the buffy coat bag 204 and transferring the buffy coat from the blood collection bag 200 to the buffy coat bag 204.

The fourth bag 206 is connected to the third bag 204 through the third transfer tube 216 and the second transfer tube 214, and is a bag for accommodating (storing) and preserving a platelet added solution. Hereinafter, the fourth bag 206 may be referred to as an "added solution bag 206". The third transfer tube 216 is a tube for connecting an inlet of the added solution bag 206 and a midway portion of the second transfer tube 214 and transferring the platelet added solution to the buffy coat bag 204 through the second transfer tube 214.

The fifth bag 208 is connected to the buffy coat bag 204 through the fourth transfer tube 218 and is a bag for accommodating a waste liquid (a mixed liquid of the blood plasma and the platelet added solution) generated when the washed buffy coat is refined. Hereinafter, the fifth bag 208 may be referred to as a "waste liquid bag 208". The fourth transfer tube 218 is a tube for connecting an inlet of the waste liquid bag 208 and an upper portion of the buffy coat bag 204 and transferring the waste liquid in the buffy coat bag 204 to the waste liquid bag 208 through the fourth transfer tube 218.

The sixth bag 210 is connected to the first bag 200 through the second transfer tube 214, the third transfer tube 216, the fifth transfer tube 220, a filter 58, and the sixth transfer tube 222, and is a bag for accommodating (storing) and preserving red cell concentrates from which a white blood cell is removed. Hereinafter, the sixth bag 210 may be referred to as a "red blood cell bag 210".

The fifth transfer tube 220 is a tube for connecting a midway portion of the third transfer tube 216 and the filter 58 and transferring the red cell concentrates from the blood collection bag 200 to the filter 58 through the second transfer tube 214 and the third transfer tube 216. The sixth transfer tube 222 is configured similarly to the above-described sixth transfer tube 34.

Figure 13:
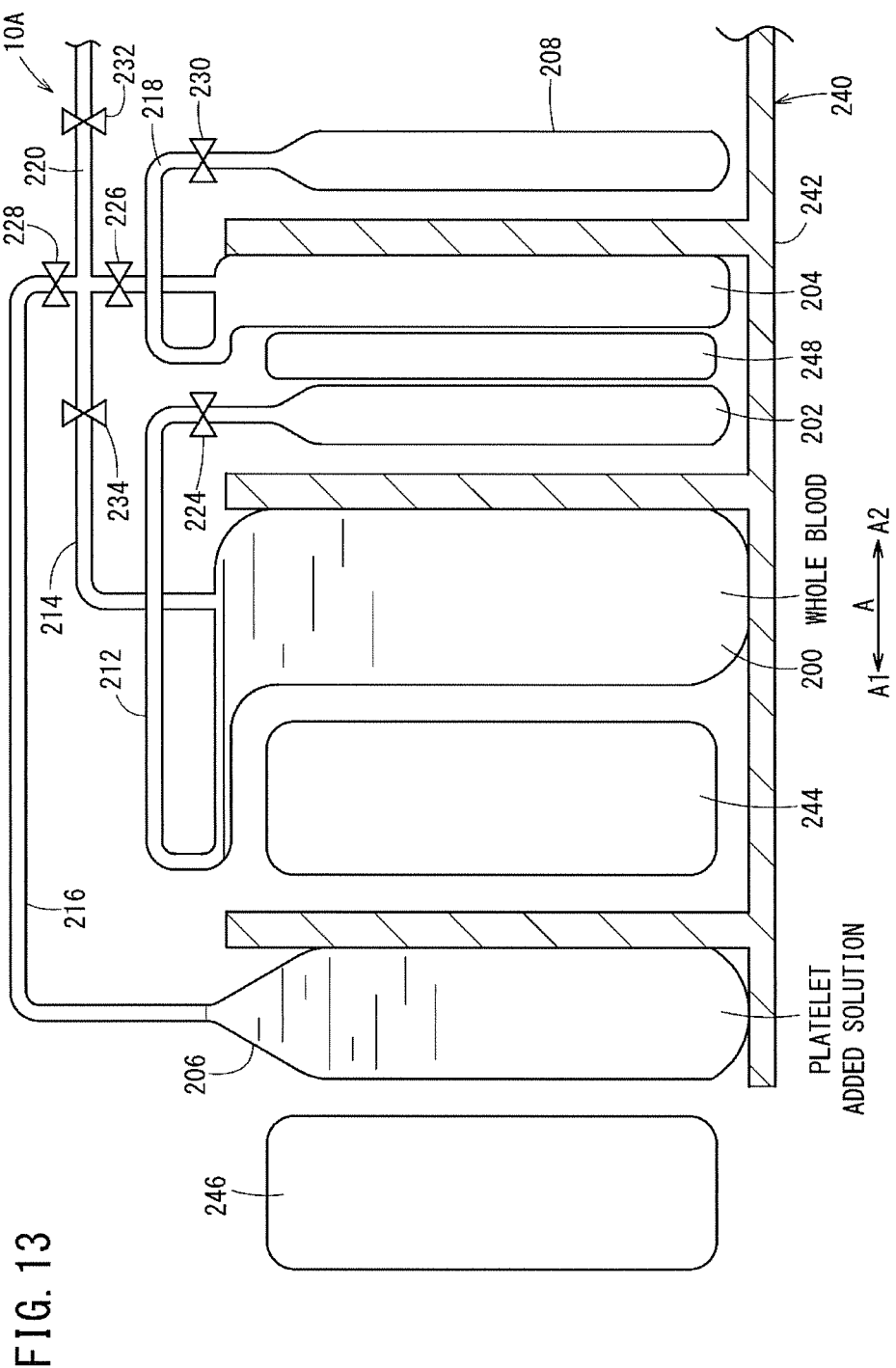
FIG. 13 is a schematic view illustrating a state of the blood bag system before a centrifugation process according to the second embodiment.

As illustrated in FIGS. 12 and 13, the blood bag system 10A includes first to sixth clamps 224, 226, 228, 230, 232, and 234 provided in a cassette (not illustrated). The first clamp 224 closes and opens a flow path of the first transfer tube 212. The second clamp 226 closes and opens a flow path of the second transfer tube 214 on a buffy coat bag 204 side of a connecting portion connected to the third transfer tube 216. The third clamp 228 closes and opens a flow path of the third transfer tube 216 on an added solution bag 206 side of a connecting portion connected to the fifth transfer tube 220. The fourth clamp 230 closes and opens the fourth transfer tube 218. The fifth clamp 232 closes and opens the fifth transfer tube 220. The sixth clamp 234 closes and opens a flow path of the second transfer tube 214 between the blood collection bag 200 and the buffy coat bag 204. Each of the first to sixth clamps 224, 226, 228, 230, 232, and 234 may be opened and closed by clamp drive means (not illustrated).

For example, the blood bag system 10A configured as described above is used by being attached to a centrifugation transfer device 240. The centrifugation transfer device 240 is configured similarly to the centrifugation transfer device 72 illustrated in FIG. 2, and includes a lid 76, a centrifugal drum 78, a unit insertion hole 80, an operation unit 88, an insert unit 242, and first to third pushers 244, 246, and 248. A plurality of chambers (not illustrated) is formed in the insert unit 242 to hold the blood collection bag 200, the blood plasma bag 202, the buffy coat bag 204, the added solution bag 206, the waste liquid bag 208, and the red blood cell bag 210.

The first pusher 244 presses the blood collection bag 200 in a rotation radial direction of the insert unit 242, the second pusher 246 presses the added solution bag 206 in the rotation radial direction of the insert unit 242, and the third pusher 248 presses the buffy coat bag 204 in the rotation radial direction of the insert unit 242.

As illustrated in FIG. 13, in the present embodiment, in a state in which the insert unit 242 is inserted into the unit insertion hole 80, the blood collection bag 200 is located in a direction of an arrow A2 of the added solution bag 206, and the blood plasma bag 202, the buffy coat bag 204, and the waste liquid bag 208 are located in the direction of the arrow A2 of the blood collection bag 200.

However, arrangement of the blood collection bag 200, the blood plasma bag 202, the buffy coat bag 204, and the waste liquid bag 208 with respect to the insert unit 242 is not limited to an example of FIG. 13, and may be freely changed. In addition, the first pusher 244 may be provided to be able to press the blood collection bag 200 in a rotation direction (circumferential direction) of the insert unit 242, the second pusher 246 may be provided to be able to press the added solution bag 206 in the rotation direction (circumferential direction) of the insert unit 242, and the third pusher 248 may be provided to be able to press the buffy coat bag 204 in the rotation direction (circumferential direction) of the insert unit 242. In other words, a scheme of arranging and driving the first to third pushers 244, 246, and 248 is not limited as long as the pushers may press the bags.

Next, a description will be given of the blood treatment method (a method of refining the washed platelet) of the present embodiment. In the present embodiment, a washed buffy coat refinement process (primary centrifugation process), a pooling process, and a white blood cell removal process (secondary centrifugation process) are successively performed.

A blood collection process, a mounting process, a centrifugation process, a first transfer process, a second transfer process and a third transfer process are performed in the washed buffy coat refinement process. Since the blood collection process is similar to that of the first embodiment, a detailed description thereof will be omitted.

In the mounting process, the blood bag system 10A is attached to the centrifugation transfer device 240 (see FIG. 2). In attachment of the blood bag system 10A to the centrifugation transfer device 240, a cassette holding the blood collection bag 200 and the first to fifth transfer tubes 212, 214, 216, 218, and 220 is attached to the insert unit 242. In this way, the blood collection bag 200 suspended and supported by the cassette is in a state of being held in a chamber (not illustrated) of the insert unit 242. In addition, the blood plasma bag 202, the buffy coat bag 204, the added solution bag 206, the waste liquid bag 208, the filter 58, and the red blood cell bag 210 are held in a chamber (not illustrated) of the insert unit 242.

Subsequently, the centrifugation process, the first transfer process, the second transfer process, and the third transfer process are automatically performed by operating the operation unit 88 after the insert unit 242 in which the blood bag system 10A is held is inserted into the unit insertion hole 80 of the centrifugation transfer device 240, and the lid 76 of the centrifugation transfer device 240 is closed. Here, FIG. 13 is a schematic view illustrating a state of the blood bag system 10A before the centrifugation process is performed (before a centrifugal force acts). The first to sixth clamps 224, 226, 228, 230, 232, and 234 are closed in advance, whereby the respective flow paths of the first through fifth transfer tubes 212, 214, 216, 218, and 220 are closed.

Figure 14:
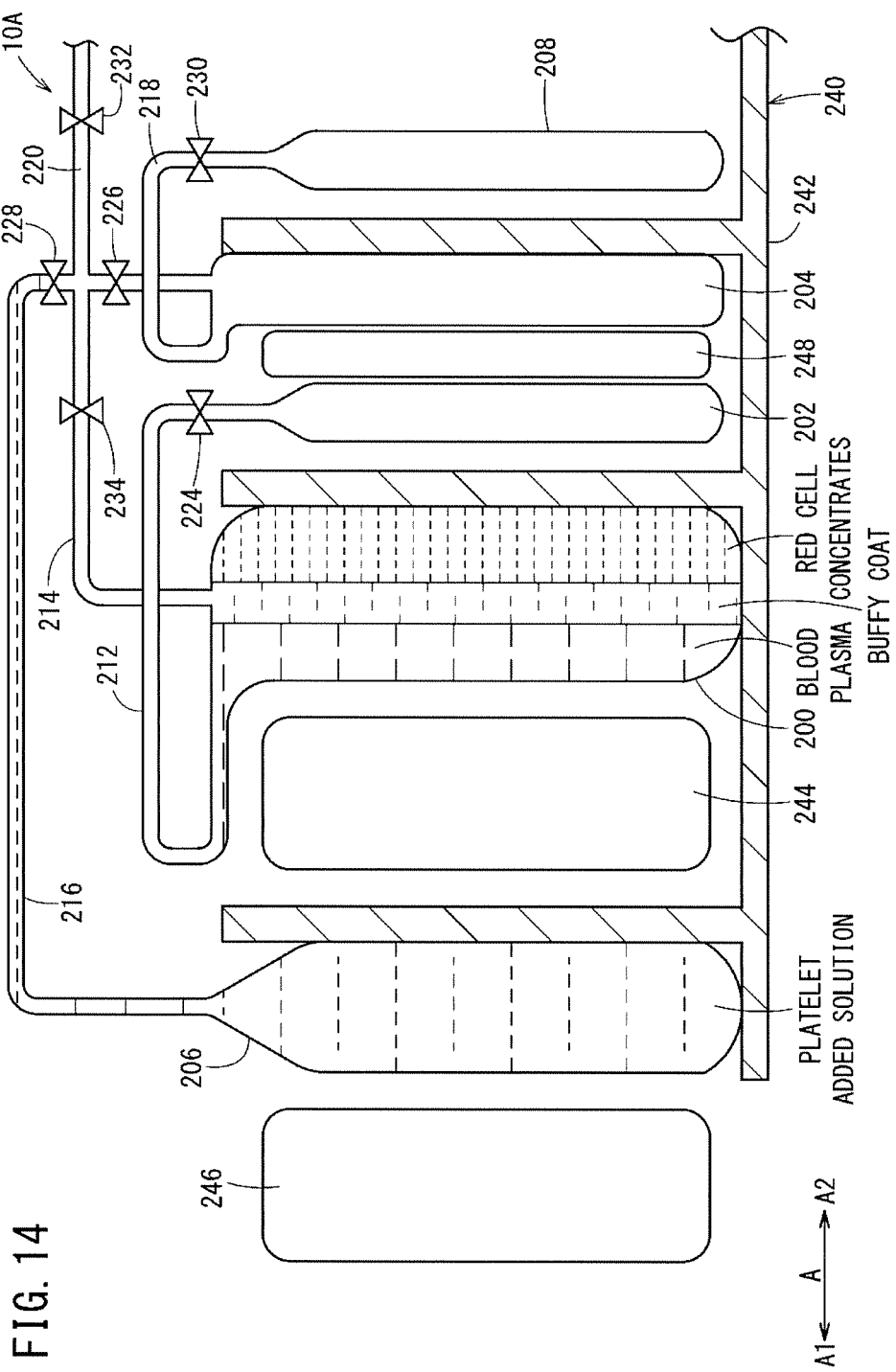
FIG. 14 is a schematic view illustrating a state of the blood bag system after the centrifugation process and before a first transfer process in a blood treatment method according to the second embodiment.

As illustrated in FIG. 14, in the centrifugation process, the centrifugation transfer device 240 rotates the centrifugal drum 78. Then, in response to the whole blood stored in the blood collection bag 200 receiving a centrifugal force, the red cell concentrates corresponding to a heavy specific gravity blood component move in a radially outward direction (the direction of the arrow A2), the blood plasma corresponding to a light specific gravity blood component moves in a radially inward direction (the direction of the arrow A1), and the buffy coat corresponding to a medium specific gravity blood component moves to an intermediate position therebetween, thereby separating the blood into three layers.

Subsequently, the centrifugation transfer device 240 proceeds to the first transfer process. In the first transfer process, while a centrifugal force is applied to the blood collection bag 200 by maintaining rotation of the centrifugal drum 78, the first clamp 224 is opened by operating the clamp drive means (not illustrated). In this way, the flow path of the first transfer tube 212 is put in an open state.

Figure 15:
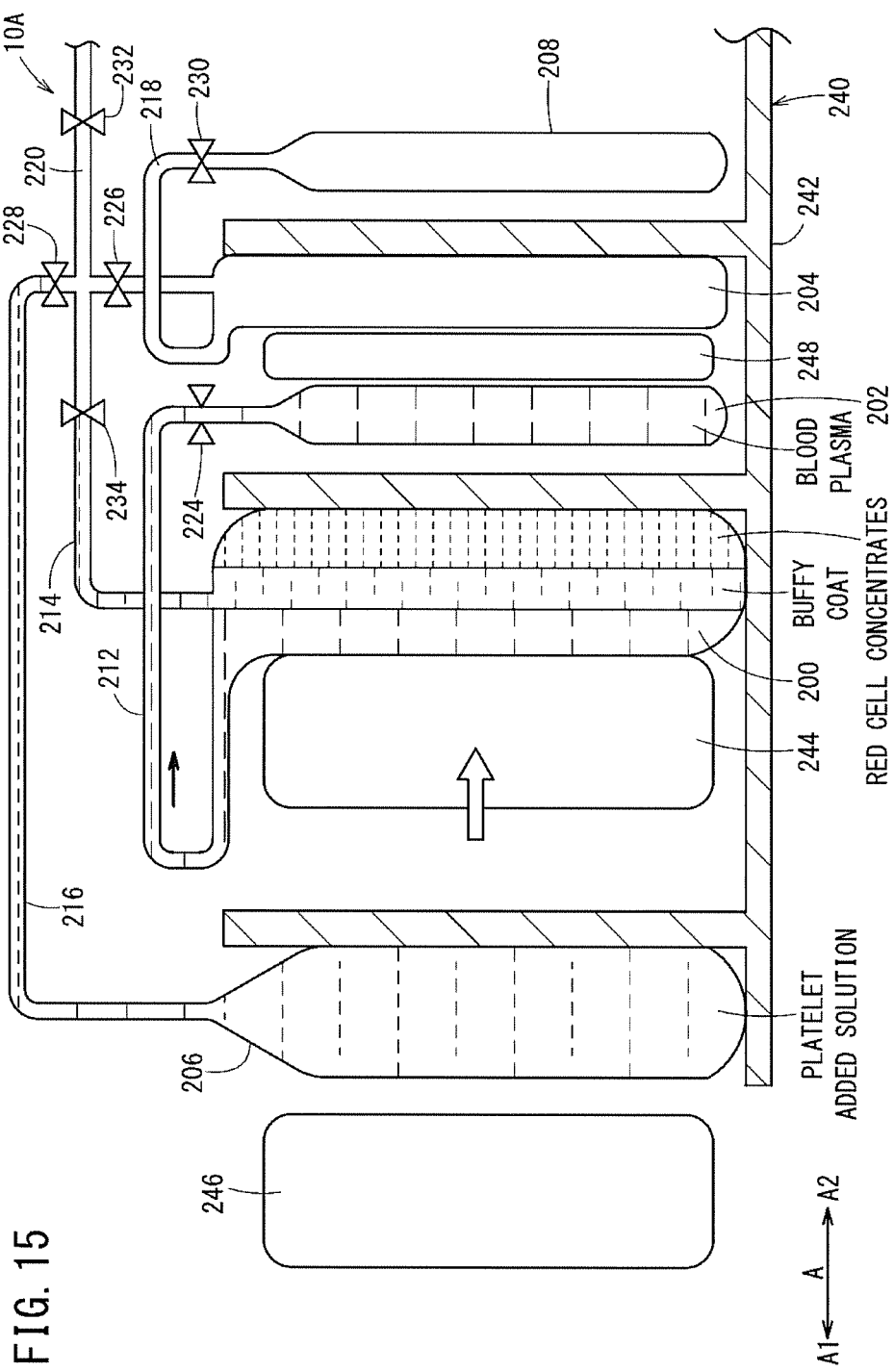
FIG. 15 is a schematic view illustrating a state of the blood bag system that transfers blood plasma from a blood collection bag to a blood plasma bag in the first transfer process according to the second embodiment.

Then, as illustrated in FIG. 15, the first pusher 244 is shifted in the centrifugal force direction, that is, the radially outward direction (the direction of the arrow A2) to press the blood collection bag 200. The blood collection bag 200 is interposed between the first pusher 244 and a wall, and thus the volume thereof is reduced. In this instance, since the first transfer tube 212 is oriented toward an inner diameter side, blood plasma located on an innermost diameter side flows out from the blood collection bag 200 to the first transfer tube 212 and flows into the blood plasma bag 202 through the first transfer tube 212.

After transfer of the blood plasma from the first transfer tube 212 to the blood plasma bag 202 is completed, the first clamp 224 is closed, and the second clamp 226 and the sixth clamp 234 are opened. In this way, the flow path of the first transfer tube 212 is closed, and the flow path of the second transfer tube 214 is put in an open state.

Figure 16:
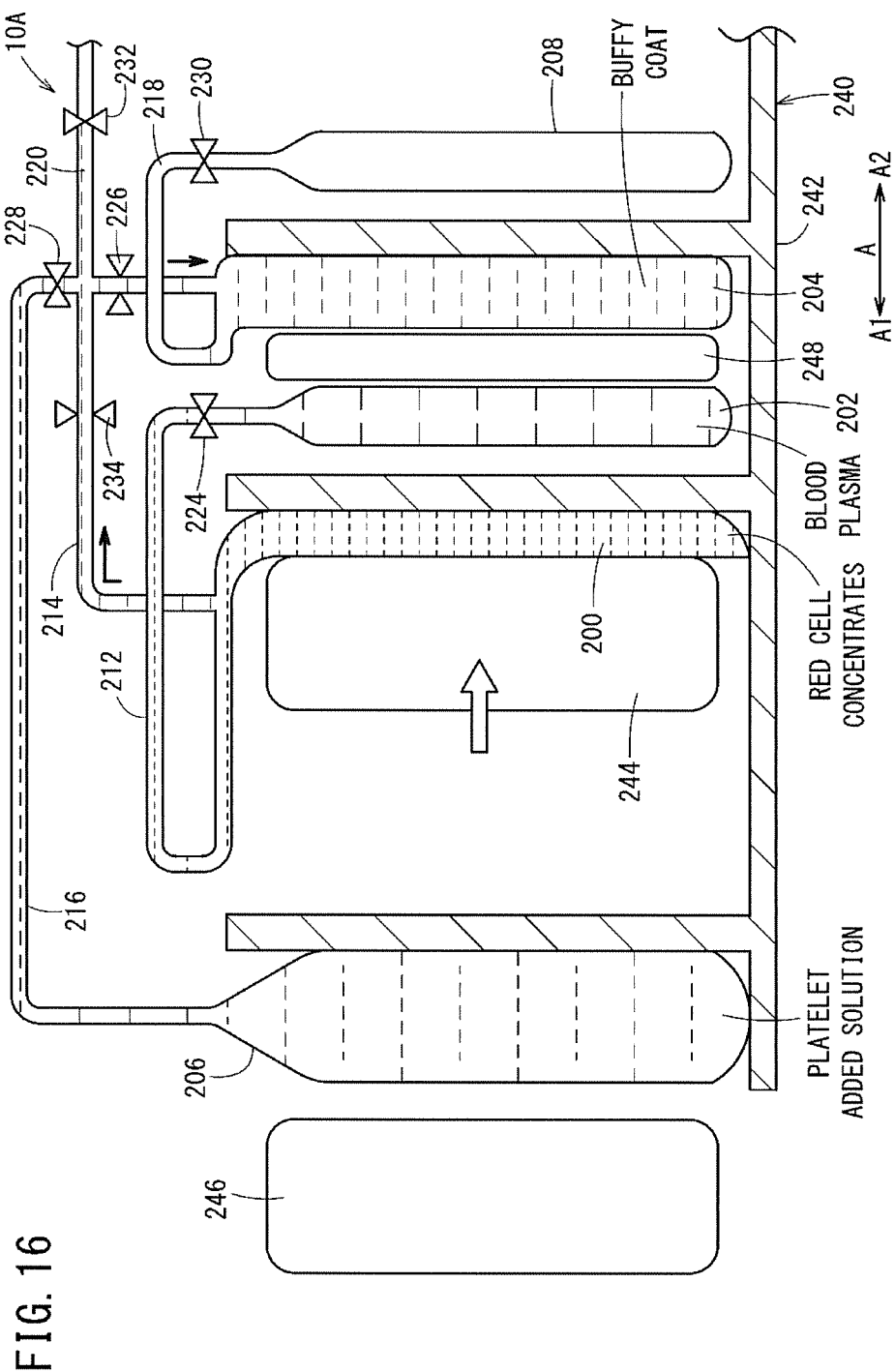
FIG. 16 is a schematic view illustrating a state of the blood bag system that transfers a buffy coat from the blood collection bag to a buffy coat bag in the first transfer process according to the second embodiment.

Subsequently, as illustrated in FIG. 16, the first pusher 244 is further shifted in the centrifugal direction to press the blood collection bag 200. In this instance, since the second transfer tube 214 is connected to an inner diameter side of a separation surface of the red cell concentrates and the buffy coat in the blood collection bag 200, the buffy coat flows out to the second transfer tube 214 from the blood collection bag 200 and flows into the buffy coat bag 204 through the second transfer tube 214. After transfer of the buffy coat from the second transfer tube 214 to the buffy coat bag 204 is completed, the sixth clamp 234 is closed.

At the time when the first transfer process is completed, the blood plasma is stored in the blood plasma bag 202, the buffy coat is stored in the buffy coat bag 204, and the red cell concentrates are left in the blood collection bag 200.

Subsequently, the centrifugation transfer device 240 proceeds to the second transfer process. In the second transfer process, while a centrifugal force is applied to the added solution bag 206 by maintaining rotation of the centrifugal drum 78, each of the third clamp 228 and the fourth clamp 230 is opened by operating the clamp drive means (not illustrated). In this way, each flow path of the third transfer tube 216 and the fourth transfer tube 218 is put in an open state.

Figure 17:
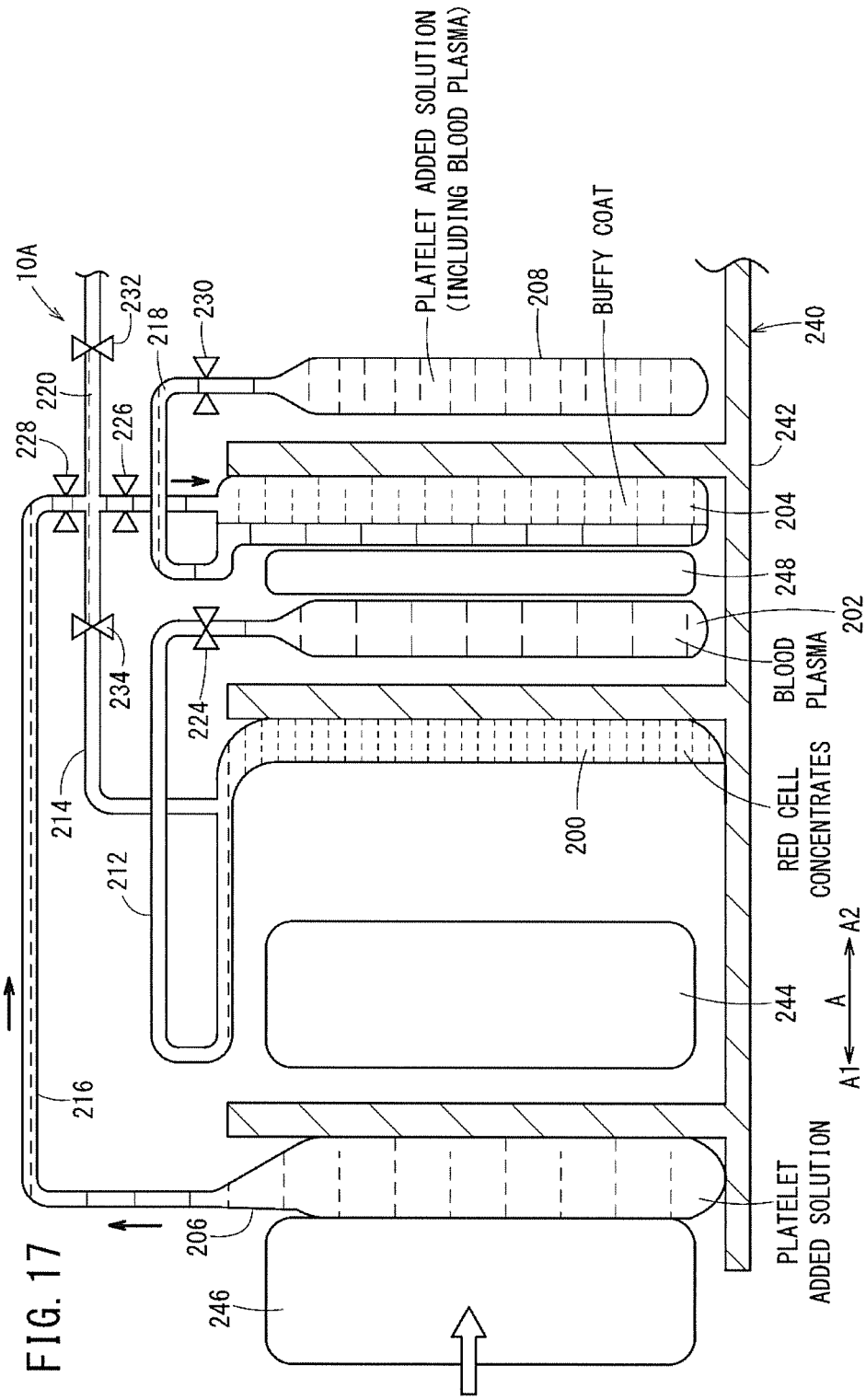
FIG. 17 is a schematic view of the blood bag system during a second transfer process according to the second embodiment.

Then, as illustrated in FIG. 17, the second pusher 246 is shifted in the centrifugal force direction, that is, the radially outward direction (the direction of the arrow A2) to press the added solution bag 206. The added solution bag 206 is interposed between the second pusher 246 and a wall, and thus the volume thereof is reduced. In this way, the platelet added solution flows out from the added solution bag 206 to the third transfer tube 216 and flows into the buffy coat bag 204 through the third transfer tube 216 and the second transfer tube 214. In this instance, since the sixth clamp 234 is closed, the platelet added solution is not mixed with the red cell concentrates stored in the blood collection bag 200.

In addition, since the specific gravity of the platelet added solution is smaller than that of the buffy coat, when the platelet added solution flows into an outer diameter side of the buffy coat bag 204 from the second transfer tube 214, blood plasma in the buffy coat is pressed to an inner diameter side (in the direction of the arrow A1) by the platelet added solution to flow out from the buffy coat bag 204 to the fourth transfer tube 218 and flow into the waste liquid bag 208 through the fourth transfer tube 218.

When a microcomputer (not illustrated) detects that the platelet added solution is transferred from the added solution bag 206 and the second pusher 246 arrives at a predetermined position, each of the second clamp 226 and the third clamp 228 is closed to close each flow path of the second transfer tube 214 and the third transfer tube 216, and the second pusher 246 is stopped. The fourth clamp 230 is kept open.

Figure 18:
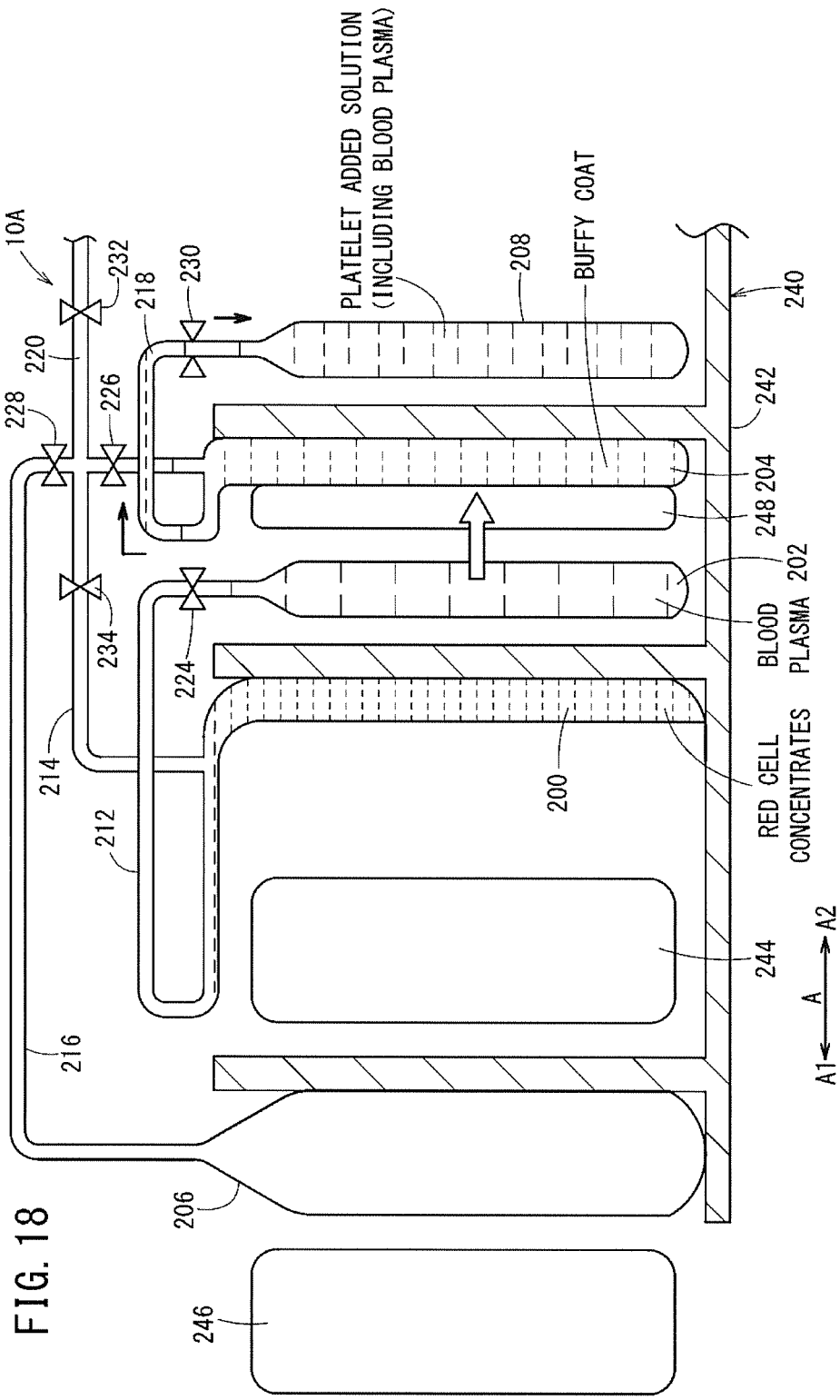
FIG. 18 is a schematic view of the blood bag system during a third transfer process according to the second embodiment.

Thereafter, the centrifugation transfer device 240 proceeds to the third transfer process. In the third transfer process, while a centrifugal force is applied to the buffy coat bag 204 by maintaining rotation of the centrifugal drum 78, the third pusher 248 is shifted in the centrifugal force direction to press the buffy coat bag 204 as illustrated in FIG. 18. The buffy coat bag 204 is interposed between the third pusher 248 and a wall, and thus the volume thereof is reduced. In this way, an extra platelet added solution in the buffy coat bag 204 flows into the waste liquid bag 208 from the buffy coat bag 204 through the fourth transfer tube 218.

When the microcomputer (not illustrated) detects that the third pusher 248 arrives at a predetermined position, the fourth clamp 230 is closed to close the flow path of the fourth transfer tube 218, and the third pusher 248 is stopped.

When the third transfer process is completed, the blood bag system 10A is removed from the insert unit 242. Further, each bag is cut off by welding and sealing each of the first to fourth transfer tubes 212, 214, 216, and 218 in the blood bag system 10A using a tube sealer and the like, and then cutting each of the first to fourth transfer tubes 212, 214, 216, and 218. In this instance, the blood collection bag 200 and the filter 58 are connected by a tube. Then, thereafter, the red cell concentrates temporarily stored in the blood collection bag 200 are passed through the filter 58 to remove the white blood cell. The red cell concentrates from which the white blood cell is removed are stored and preserved in the red blood cell bag 210.

The pooling process and the white blood cell removal process are the same as those of the first embodiment, and thus a detailed description thereof will be omitted.

According to the present embodiment, the same effect as that of the first embodiment described above may be obtained. In more detail, in a transfer completed state in which the blood plasma and the buffy coat obtained by centrifuging the whole blood (content liquid) in the blood collection bag 200 are transferred to the blood plasma bag 202 and the buffy coat bag 204, respectively, the platelet added solution in the added solution bag 206 is transferred to an outer diameter side of the buffy coat bag 204 on which a centrifugal force acts. In this way, since the blood plasma remaining in the buffy coat may be discharged from the buffy coat bag 204 by the platelet added solution, the washed buffy coat may be obtained. Therefore, it is possible to securely and efficiently obtain the washed buffy coat having a sufficiently low content rate of blood plasma in the buffy coat bag 204.

The blood bag system and the blood treatment method according to the invention are not limited to the above-described embodiments, and various configurations may be adopted without departing from the subject matter of the invention.

REFERENCE SIGNS LIST 10, 10A blood bag system
12, 200 blood collection bag (first bag)
14, 202 blood plasma bag (second bag)
16 first red blood cell bag (third bag)
18, 206 added solution bag (fourth bag)
20, 208 waste liquid bag (fifth bag)
22 second red blood cell bag (sixth bag)
24, 212 first transfer tube
26, 214 second transfer tube
28, 216 third transfer tube
30, 218 fourth transfer tube
32, 220 fifth transfer tube
34, 222 sixth transfer tube
64, 224 first clamp
66, 226 second clamp
68, 228 third clamp
70, 230 fourth clamp
72, 240 centrifugation transfer device
204 buffy coat bag (third bag)
210 red blood cell bag (sixth bag)

The invention claimed is:

1. A blood bag system comprising:
a first bag for storing whole blood or a blood component;
a second bag and a third bag for storing two blood components, respectively, from among a light specific gravity blood component, a medium specific gravity blood component, and a heavy specific gravity blood component obtained by centrifuging a content liquid in the first bag, wherein a specific gravity of the medium specific gravity blood component is higher than a specific gravity of the light specific gravity blood component and lower than a specific gravity of the heavy specific gravity blood component;
a first transfer tube for connecting the first bag and the second bag to each other and transferring one of the two blood components from the first bag to the second bag;
a second transfer tube for connecting the first bag and the third bag to each other and transferring the other of the two blood components from the first bag to the third bag
a fourth bag storing an added solution; and
a third transfer tube for transferring the added solution from the fourth bag to the medium specific gravity blood component,
wherein a centrifugal force acts in a transfer completed state in which the two blood components are separately transferred to the second bag and the third bag, respectively, and the added solution is transferred from the fourth bag to the medium specific gravity blood component through the third transfer tube, thereby discharging the light specific gravity blood component remaining in the medium specific gravity blood component.

2. The blood bag system according to claim 1, wherein in the transfer completed state, the medium specific gravity blood component remains in the first bag, the light specific gravity blood component is stored in the second bag, and the heavy specific gravity blood component is stored in the third bag, and the third transfer tube is a tube for transferring the added solution from the fourth bag to the first bag.

3. The blood bag system according to claim 2, further comprising:
a fifth bag that stores a waste liquid containing the light specific gravity blood component and the added solution discharged from the first bag; and
a fourth transfer tube for transferring the waste liquid discharged from the first bag to the fifth bag.

4. The blood bag system according to claim 3, wherein the third transfer tube connects the second transfer tube and the fourth bag to each other, and the fourth transfer tube connects the first transfer tube and the fifth bag to each other.

5. The blood bag system according to claim 4, further comprising:
a first clamp that closes and opens a second bag side of a connecting portion connected to the fourth transfer tube in the first transfer tube;
a second clamp that closes and opens a third bag side of a connecting portion connected to the third transfer tube in the second transfer tube;
a third clamp that closes and opens the third transfer tube; and a fourth clamp that closes and opens the fourth transfer tube.

6. The blood bag system according to claim 1, wherein in the transfer completed state, the heavy specific gravity blood component remains in the first bag, the light specific gravity blood component is stored in the second bag, and the medium specific gravity blood component is stored in the third bag, and the third transfer tube is a tube for transferring the added solution from the fourth bag to the third bag.

7. The blood bag system according to claim 6, further comprising:
a fifth bag that stores a waste liquid containing the light specific gravity blood component and the added solution discharged from the third bag; and
a fourth transfer tube for transferring the waste liquid discharged from the third bag to the fifth bag.

8. A blood treatment method comprising:
a centrifugation process of centrifuging whole blood or a blood component in a first bag into a light specific gravity blood component, a medium specific gravity blood component, and a heavy specific gravity blood component for each specific gravity, wherein a specific gravity of the medium specific gravity blood component is higher than a specific gravity of the light specific gravity blood component and lower than a specific gravity of the heavy specific gravity blood component;
a first transfer process of transferring one of two blood components from among the light specific gravity blood component, the medium specific gravity blood component, and the heavy specific gravity blood component from the first bag to a second bag through a first transfer tube, and transferring the other one of the two blood components from the first bag to a third bag through a second transfer tube; and
a second transfer process of transferring an added solution stored in a fourth bag to the medium specific gravity blood component through a third transfer tube while a centrifugal force is applied after the first transfer process to discharge the light specific gravity blood component remaining in the medium specific gravity blood component, thereby obtaining a washed medium specific gravity blood component.

9. The blood treatment method according to claim 8, wherein in the first transfer process, the light specific gravity blood component is transferred to the second bag, and the heavy specific gravity blood component is transferred to the third bag, thereby leaving the medium specific gravity blood component in the first bag, and in the second transfer process, the added solution stored in the fourth bag is transferred to the first bag through the third transfer tube.

10. The blood treatment method according to claim 9, wherein in the second transfer process, the first bag is disposed in a centrifugal force direction from the fourth bag.

11. The blood treatment method according to claim 10, wherein in the second transfer process, the added solution in the fourth bag is transferred to the first bag through the third transfer tube by pressing the fourth bag.

12. The blood treatment method according to claim 11, further comprising:
a third transfer process of transferring a waste liquid containing the light specific gravity blood component and the added solution discharged from the first bag to a fifth bag through a fourth transfer tube after the second transfer process.

13. The blood treatment method according to claim 12, wherein in the third transfer process, a part of the added solution in the first bag is transferred to the fifth bag by pressing the first bag in a state in which the third transfer tube is closed.

14. The blood treatment method according to claim 13, wherein in the second transfer process, the added solution is introduced to an outer diameter side of the first bag.

15. The blood treatment method according to claim 14, further comprising:
a pooling process of collecting the washed medium specific gravity blood component in a plurality of bags in a pooling bag; and
a white blood cell removal process of removing a white blood cell from the washed medium specific gravity blood component in the pooling bag.

16. The blood bag system according to claim 1, wherein the light specific gravity blood component corresponds to blood plasma, the medium specific gravity blood component corresponds to buffy coat, and the heavy specific gravity blood component corresponds to red cell concentrates.

17. The blood treatment method according to claim 8, wherein the light specific gravity blood component corresponds to blood plasma, the medium specific gravity blood component corresponds to buffy coat, and the heavy specific gravity blood component corresponds to red cell concentrates.

18. A blood bag system comprising:
a first bag for storing whole blood or a blood component;
a second bag and a third bag for storing two blood components, respectively, from among a first blood component, a second blood component, and a third blood component obtained by centrifuging a content liquid in the first bag;
a first transfer tube for connecting the first bag and the second bag to each other and transferring one blood component of the two blood components from the first bag to the second bag;
a second transfer tube for connecting the first bag and the third bag to each other and transferring the other blood component of the two blood components from the first bag to the third bag;
a fourth bag storing an added solution; and
a third transfer tube for transferring the added solution from the fourth bag to the second blood component,
wherein a centrifugal force acts in a transfer completed state in which the two blood components are separately transferred to the second bag and the third bag, respectively, and the added solution is transferred from the fourth bag to the second blood component through the third transfer tube, thereby discharging the first blood component remaining in the second blood component.

19. The blood bag system according to claim 18, wherein a specific gravity of the second blood component is higher than a specific gravity of the first blood component and lower than a specific gravity of the third blood component.

20. The blood bag system according to claim 19, wherein the first blood component corresponds to blood plasma, the second blood component corresponds to buffy coat, and the third blood component corresponds to red cell concentrates.

* * * * *